United States Patent
Ikeyama et al.

(10) Patent No.: US 11,707,488 B2
(45) Date of Patent: *Jul. 25, 2023

(54) ROR1-POSITIVE MESENCHYMAL STEM CELLS AND METHOD FOR PREPARING SAME, PHARMACEUTICAL COMPOSITION CONTAINING ROR1-POSITIVE MESENCHYMAL STEM CELLS AND METHOD FOR PREPARING SAME, AND METHOD FOR PREVENTING OR TREATING DISEASE USING ROR1-POSITIVE MESENCHYMAL STEM CELLS

(71) Applicant: ROHTO PHARMACEUTICAL CO., LTD., Osaka (JP)

(72) Inventors: Yoshifumi Ikeyama, Osaka (JP); Hiroyuki Nishida, Osaka (JP); Tomohiro Tsuda, Osaka (JP); Eiko Uno, Osaka (JP); Masayo Yumoto, Osaka (JP); Kazuma Suda, Osaka (JP); Mihoko Yoshino, Osaka (JP); Xuan Trung Ngo, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 301 days.

This patent is subject to a terminal disclaimer.

(21) Appl. No.: 15/755,859

(22) PCT Filed: Aug. 29, 2016

(86) PCT No.: PCT/JP2016/075251
§ 371 (c)(1),
(2) Date: Feb. 27, 2018

(87) PCT Pub. No.: WO2017/038784
PCT Pub. Date: Mar. 9, 2017

(65) Prior Publication Data
US 2018/0333436 A1    Nov. 22, 2018

Related U.S. Application Data

(60) Provisional application No. 62/268,146, filed on Dec. 16, 2015, provisional application No. 62/211,390, filed on Aug. 28, 2015.

(51) Int. Cl.
*A61K 35/28* (2015.01)
*C12N 5/0775* (2010.01)

(52) U.S. Cl.
CPC ............ *A61K 35/28* (2013.01); *C12N 5/0662* (2013.01); *C12N 2501/998* (2013.01); *C12N 2510/00* (2013.01); *Y02A 50/30* (2018.01)

(58) Field of Classification Search
CPC .................. A61K 35/28; C12N 5/0662; C12N 2501/998; C12N 2510/00; Y02A 50/30; A61P 3/00; A61P 9/00; A61P 19/00; A61P 35/00; A61P 1/00
USPC ....................................................... 424/93.21
See application file for complete search history.

(56) References Cited

U.S. PATENT DOCUMENTS

| | | | |
|---|---|---|---|
| 9,758,591 B2 | 9/2017 | Kipps et al. | |
| 2006/0233766 A1 | 10/2006 | Messina et al. | |
| 2007/0264269 A1 | 11/2007 | Harmon et al. | |
| 2011/0262393 A1 | 10/2011 | Yang et al. | |
| 2012/0244129 A1 | 9/2012 | Dezawa et al. | |
| 2012/0269774 A1 | 10/2012 | Ichim et al. | |
| 2015/0024966 A1 | 1/2015 | Brodie et al. | |
| 2016/0114183 A1 | 4/2016 | Bartholomew et al. | |
| 2018/0066231 A1 | 3/2018 | Ikeyama et al. | |
| 2018/0333436 A1 | 11/2018 | Ikeyama et al. | |
| 2019/0117701 A1 | 4/2019 | Ikeyama et al. | |
| 2020/0069740 A1* | 3/2020 | Hasegawa | A61P 13/12 |

FOREIGN PATENT DOCUMENTS

| | | |
|---|---|---|
| EP | 3450548 A1 | 3/2019 |
| JP | 2007-528705 A | 10/2007 |
| JP | 2008-525489 A | 7/2008 |
| JP | 2009-519978 A | 5/2009 |
| JP | 2012508733 A | 4/2012 |
| JP | 2012157263 A | 8/2012 |
| WO | 2005001080 A3 | 3/2005 |
| WO | 2014/031174 A1 | 2/2014 |
| WO | 2014-203267 A2 | 12/2014 |

(Continued)

OTHER PUBLICATIONS

Cui et al. "Targeting ROR1 inhibits epithelial-mesenchymal transition and metastasis." Cancer research 73.12 (2013): 3649-3660.*

(Continued)

*Primary Examiner* — Janet L Epps-Smith
*Assistant Examiner* — Alexander W Nicol
(74) *Attorney, Agent, or Firm* — Osha Bergman Watanabe & Burton LLP

(57) ABSTRACT

An object of the present invention is to provide novel mesenchymal stem cells demonstrating superior therapeutic effects against various diseases, a novel pharmaceutical composition containing these mesenchymal stem cells, and a method for preparing the same. The present invention relates to ROR1-positive mesenchymal stem cells. The ROR1-positive mesenchymal stem cells are preferably positive for CD29, CD73, CD90, CD105 and CD166 and are derived from umbilical cord or adipose tissue.

2 Claims, 18 Drawing Sheets

(56) References Cited

FOREIGN PATENT DOCUMENTS

| WO | 2015-121859 A1 | 8/2015 |
|---|---|---|
| WO | 2016136986 A1 | 9/2016 |
| WO | 2017038784 A1 | 3/2017 |

OTHER PUBLICATIONS

Zhang et al. "Ovarian cancer stem cells express ROR1, which can be targeted for anti-cancer-stem-cell therapy." Proceedings of the National Academy of Sciences 111.48 (2014): 17266-17271.*
Kern et al. "Comparative analysis of mesenchymal stem cells from bone marrow, umbilical cord blood, or adipose tissue." Stem cells 24.5 (2006): 1294-1301.*
Mahdi Shabani et al. "Receptor tyrosine kinase-like orphan receptor 1: a novel target for cancer immunotherapy", Expert Opinion on Theraputic Targets, vol. 19, No. 7, Apr. 2, 2015, pp. 941-955. (16 pages).
Hojjat-Farsangi Mohammad et al. "The receptor tyrosine kinase ROR1—An oncofetal antigen for targeted cancer therapy", Seminars in Cancer Biology, Saunders Scientific Publications, Philadelphia, PA, US, vol. 29, Jul. 25, 2014, pp. 21-31 (11 pages).
Extended European Search Report issued in European Application No. 16841816.8, dated Mar. 4, 2019 (8 pages).
S. Cai et al., "Activation of Wnt/ß-catenin signalling promotes mesenchymal stem cells to repair injured alveolar epithelium induced by lipopolysaccharide in mice," Stem Cell Research & Therapy, p. 2, vol. 6, 2015 (11 pages).
International Search Report issued in International Application No. PCT/JP2018/009019; dated Jun. 12, 2018 (1 page).
Written Opinion of the International Searching Authority issued in International Application No. PCT/JP2018/009019 dated Jun. 12, 2018 (7 pages).
International Search Report issued in PCT/JP2016/075251 dated Nov. 22, 2016 (1 page).
Written Opinion of the International Searching Authority issued in PCT/JP2016/075251 dated Nov. 22, 2016 (4 pages).
Hudecek, M. et al.; "The B-cell tumor-associated antigen ROR1 can be targeted with T cells modified to express a ROR1-specific chimeric antigen receptor"; Blood, vol. 116, No. 22, Nov. 2010, pp. 4532-4541 (11 pages).
Zhang, S. et al.; "Ovarian cancer stem cells express ROR1, which can be targeted for anti-cancer-stem-cell therapy" Proc. Natl. Acad. Sci. USA,, vol. 111, No. 48, Dec. 2, 2014, pp. 17266-17271 (6 pages).
T. Mizoguchi, "The Bone", Dec. 26, 2014, vol. 28, pp. 367-371, with Partial English translation (7 pages).
S. Sotome, "Artificial Bones", Artificial organs, 2014 years, Japanese Society for Artificial Organs, vol. 43, No. 3, pp. 185-188, with Partial English translation (6 pages).
T. Arahira et al., "Effects of Proliferation and Differentiation of Mesenchymal Stem Cells on Compressive Mechanical Behavior of Collagen/ß-TCP Composite Scaffold", J. Mech. Behav. Biomed. Mater., 2014, vol. 39, pp. 218-230 (14 pages).
H. J. Oh et al., "Analysis of cell growth and gene expression of porcine adipose tissue-derived mesenchymal stem cells as nuclear donor cell", Develop. Growth Differ., 2014, vol. 56, pp. 595-604 (11 pages).
Y. Wang et al., "Activation of Liver X Receptor Improves Viability of Adipose-Derived Mesenchymal Stem Cells to Attenuate Myocardial Ischemia Injury Through TLR4/NF-kB and Keap-1/Nrf-2 Signaling Pathways", Antioxid., Redox Signal., 2014, vol. 21, No. 18, pp. 2543-2557 (16 pages).
Y. Wang et al., "Human Adipose-Derived Mesenchymal Stem Cells are Resistant to HBV Infection during Differentiation into Hepatocytes in Vitro", Int. J. Mol. Sci., 2014, vol. 15, pp. 6096-6110 (16 pages).
Office Action issued in Japanese Application No. 2017-538029, dated Aug. 4, 2020 (13 pages).
Restriction Requirement issued in U.S. Appl. No. 16/491,974, dated Aug. 24, 2020 (10 pages).
Office Action issued in U.S. Appl. No. 16/491,974, dated Dec. 18, 2020 (12 pages).
Office Action issued in corresponding Chinese Application No. 201680062889.3, dated Dec. 7, 2020 (11 pages).
Z. Du et al., Collection of Papers at the 9th National Conference on Biomedical Stereology, the 12th Whole Army Academic Conference on Military Pathology,and the 8th Whole Army Academic Conference on Quantitative Pathology, pp. 249-251 (8 pages).
J-O. Ahn et al., "Human Adipose Tissue-derived Mesenchymal Stem Cells Inhibit Melanoma Growth In Vitro and In Vivo", Anticancer Research, Jan. 2015, vol. 35, No. 1, pp. 159-168 (1 page).
Office Action issued in corresponding European Application No. 16841816.8, dated Feb. 1, 2021 (5 pages).
C. Campagnoli et al., "Identification of mesenchymal stem/progenitor cells in human first-trimester fetal blood, liver, and bone marrow", The American Society of Hematology, Blood, Oct. 15, 2001, vol. 98, No. 8, pp. 2396-2402 (7 pages).
Extended European Search Report issued in European Application No. 18764473.7, dated Dec. 8, 2020 (9 pages).
D. Alvarez et al., "Regenerative medicine in the treatment of idiopathic pulmonary fibrosis: current position", Apr. 1, 2015, Stem Cells and Cloning: Advances and Applications, vol. 8, pp. 61-65 (5 pages).
Office Action issued in corresponding European Application No. 18764473.7, dated Dec. 15, 2021 (5 pages).
Examination Report issued in corresponding European Application No. 16841816.8, dated Oct. 12, 2021 (6 pages).
Cai et al. "Matrices secreted during simultaneous osteogenesis and adipogenesis of mesenchymal stem cells affect stem cells differentiation." Acta biomaterialia 35 (2016):185-193 (Year: 2016) (9 pages).
Pasquinelli et al."Mesenchymal stem cell interaction with a nonwoven hyaluronan-based scaffold suitable for tissue repair." Journal of anatomy 213.5 (2008):520-530 (11 pages).
Office Action issued in U.S. Appl. No. 16/491,974; dated Jun. 28, 2022 (24 pages).

* cited by examiner

UC-MSC a) Recommended medium                b) Formulated medium

AD-MSC c) Recommended medium                d) Formulated medium

UC-MSC a) Recommended medium    b) Formulated medium

AD-MSC c) Recommended medium    d) Formulated medium

ROR1-POSITIVE MESENCHYMAL STEM CELLS AND METHOD FOR PREPARING SAME, PHARMACEUTICAL COMPOSITION CONTAINING ROR1-POSITIVE MESENCHYMAL STEM CELLS AND METHOD FOR PREPARING SAME, AND METHOD FOR PREVENTING OR TREATING DISEASE USING ROR1-POSITIVE MESENCHYMAL STEM CELLS

TECHNICAL FIELD

The present invention relates to ROR1-positive mesenchymal stem cells and a method for preparing the same, a pharmaceutical composition containing ROR1-positive mesenchymal stem cells and a method for preparing the same, and a method for preventing or treating disease using ROR1-positive mesenchymal stem cells.

BACKGROUND ART

In recent years, advances have been made in the development of pharmaceuticals using body cells or tissue, and research has been conducted in the field of regenerative medicine, both of which are attracting considerable attention. In particular, research has been proceeding at an accelerated pace in the areas of ES cells and iPS cells for use in organ regeneration technology and drug development screening. On the other hand, cell therapy, which uses somatic stem cells (mesenchymal stem cells) isolated from bone marrow, adipose tissue or umbilical cord, is attracting attention as having the highest potential for realization among forms of regenerative medicine since it uses the inherent functions of somatic stem cells to repair tissue damaged by disease or other causes, and is being targeted for research for this reason. Generally speaking, somatic stem cells (mesenchymal stem cells) are not able to differentiate into all organs and tissue, but rather are known to only differentiate into specific tissues and organs.

In addition, not only are somatic stem cells (mesenchymal stem cells) effective for repairing damaged tissue as previously described, but are also known to have therapeutic effects on various diseases. For example, somatic stem cells (mesenchymal stem cells) originating in umbilical cord tissue are known to demonstrate an effect that suppresses reverse immune reactions (graft versus host disease (GVHD)) in transplant recipients having unsuitable histocompatibility with the transplant donor (see Patent Document 1), mesenchymal stem cells derived from specific umbilical cord tissue are known to be able to be used to treat Parkinson's disease (see Patent Document 2), and mesenchymal stem cells derived from specific umbilical cord tissue are known to demonstrate a therapeutic effect on diseases of the circulatory system (see Patent Document 3). However, the therapeutic effects of these mesenchymal stem cells cannot be said to be adequate.

PRIOR ART DOCUMENTS

Patent Documents

Patent Document 1: JP-T 2009-519978
Patent Document 2: JP-T 2008-525489
Patent Document 3: JP-T 2007-528705

DISCLOSURE OF THE INVENTION

Problems to be Solved by the Invention

With the foregoing in view, an object of the present invention is to provide novel mesenchymal stem cells demonstrating superior therapeutic effects against various diseases and a method for preparing these mesenchymal stem cells, a novel pharmaceutical composition containing these mesenchymal stem cells and a method for preparing this pharmaceutical composition, and a method for preventing or treating disease using ROR1-positive mesenchymal stem cells.

Means for Solving the Problems

As a result of conducting extensive studies to solve the aforementioned problems, the inventors of the present invention found that a pharmaceutical composition containing certain specific mesenchymal stem cells demonstrates superior therapeutic effects against various diseases, thereby leading to completion of the present invention. Namely, the gist of the present invention is as indicated below.

(1) ROR1-positive mesenchymal stem cells.
(2) The mesenchymal stem cells described in (1), which are positive for CD29, CD73, CD90, CD105 and CD166.
(3) The mesenchymal stem cells described in (1) or (2), which are derived from umbilical cord or adipose tissue.
(4) A pharmaceutical composition containing the mesenchymal stem cells described in any one of (1) to (3) and/or culture supernatant thereof.
(5) The pharmaceutical composition described in (4), wherein, in the case the pharmaceutical composition contains ROR1-positive mesenchymal stem cells, the ratio of ROR1-positive mesenchymal stem cells is 70% or more of all mesenchymal stem cells contained in the pharmaceutical composition.
(6) The pharmaceutical composition described in (4) or (5), wherein, in the case the pharmaceutical composition contains ROR1-positive mesenchymal stem cells, the ratio of ROR1-positive mesenchymal stem cells is 90% or more of all mesenchymal stem cells contained in the pharmaceutical composition.
(7) The pharmaceutical composition described in any one of (4) to (6), which is used to prevent or treat a disease selected from the group consisting of cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases and kidney diseases.
(8) The pharmaceutical composition described in any one of (4) to (7), which is used to prevent or treat diseases caused by a decrease in the barrier function of the epithelium or endothelium, or diseases in which IL-1 is involved.
(9) The pharmaceutical composition described in (8), wherein the decrease in barrier function is caused by a decrease in the function of tight junctions in the epithelial or endothelial cell layer.
(10) The pharmaceutical composition described in any one of (4) to (6), which is used to inhibit the infiltration and/or metastasis of cancer cells.
(11) The pharmaceutical composition described in any one of (4) to (10), which is a mitochondrial transfer agent.

(12) A method for preparing ROR1-positive mesenchymal stem cells, including a step for inducing, concentrating or isolating and sorting ROR1-positive mesenchymal stem cells.

(13) A method for preparing a pharmaceutical composition used to prevent or treat disease, including a step for inducing, concentrating or isolating and sorting ROR1-positive mesenchymal stem cells.

(14) The method for preparing a pharmaceutical composition described in (13), wherein the disease is selected from the group consisting of cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases and kidney diseases.

(15) A method for preventing or treating a disease selected from the group consisting of cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases and kidney diseases, which uses ROR1-positive mesenchymal stem cells.

Effects of the Invention

ROR1-positive stem cells are characterized as cells which, in addition to demonstrating superior action that inhibits the production of inflammatory cytokines from macrophages and other immune cells, action that enhances barrier function, migratory capacity and mitochondrial transfer capacity, are resistant to oxidative stress and less susceptible to damage. In addition, a culture supernatant of ROR1-positive mesenchymal stem cells demonstrates similar functions. Consequently, the pharmaceutical composition of the present invention, which contains ROR1-positive mesenchymal stem cells and/or a culture supernatant thereof, demonstrates superior therapeutic effects against various diseases such as cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases or kidney diseases.

BEST MODE FOR CARRYING OUT THE INVENTION

Figure 1:
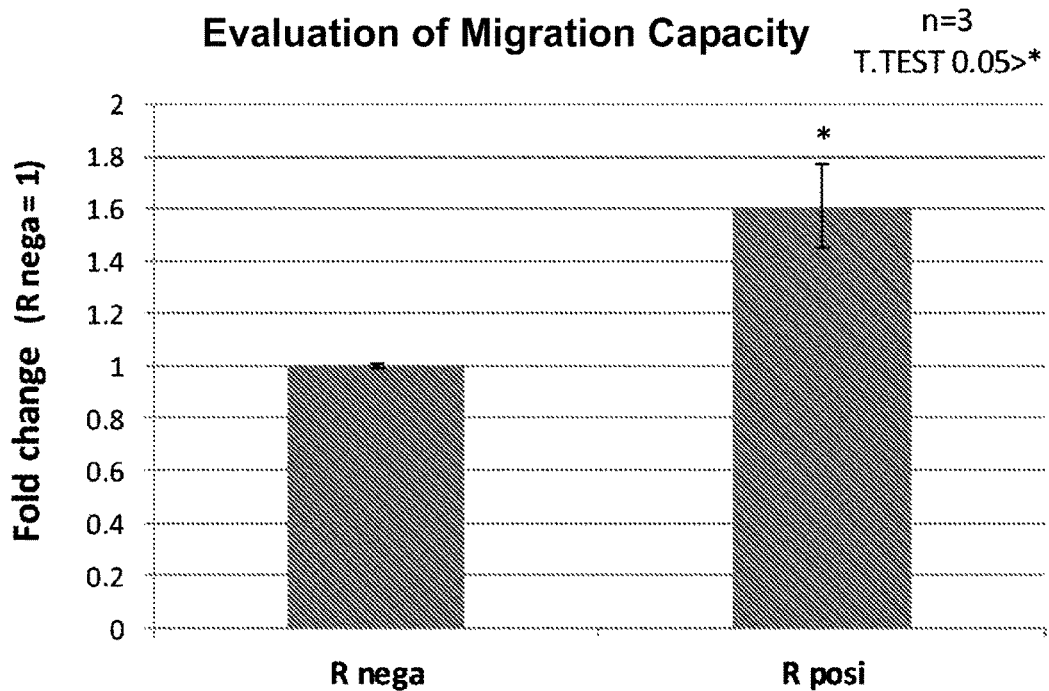
FIG. 1 is a bar graph indicating the migratory capacity of ROR1-positive mesenchymal stem cells.

ROR1-positive stem cells are characterized as cells which, in addition to demonstrating action that inhibits the production of IL-6 and other inflammatory cytokines, action that enhances barrier function, migratory capacity and mitochondrial transfer capacity, are resistant to oxidative stress and less susceptible to damage. In addition, ROR1-positive mesenchymal stem cells maintain an undifferentiated state while simultaneously efficiently differentiating into cells having a target function under differentiation conditions. In addition, a culture supernatant of ROR1-positive mesenchymal stem cells demonstrates similar functions. Thus, the pharmaceutical composition of the present invention containing these ROR1-positive mesenchymal stem cells and/or a culture supernatant thereof demonstrates superior therapeutic effects against various diseases. The following provides an explanation of the ROR1-positive mesenchymal stem cells and the pharmaceutical composition containing the same of the present invention.

[ROR1-Positive Mesenchymal Stem Cells]

In the present invention, mesenchymal stem cells refer to cells having the capacity to differentiate into cells belonging to the mesenchyme system such as osteocytes, cardiac myocytes, chondrocytes, tendon cells or adipocytes, and are able to grow while maintaining this capacity to differentiate. Examples of mesenchymal stem cells include mesenchymal stem cells derived from bone marrow, adipose tissue, blood, periosteum, dermis, umbilical cord, placenta, amnion, chorion, deciduous membrane, muscle, endometrium, dermis, dental follicle, periodontal membrane, dental pulp or tooth germ, preferably include mesenchymal stem cells derived from umbilical cord, adipose tissue or bone marrow, more preferably include mesenchymal stem cells derived from umbilical cord or adipose tissue, and even more preferably include mesenchymal stem cells derived from umbilical cord. Here, the term "derived" indicates that the aforementioned cells have been acquired, grown or manipulated in vitro from tissue serving as a supply source thereof. Furthermore, the ROR1-positive mesenchymal stem cells of the present invention may be aggregates of the aforementioned mesenchymal stem cells, may contain multiple types of mesenchymal stem cells having mutually different properties, or may be aggregates of substantially homogeneous mesenchymal stem cells.

The mesenchymal stem cells of the present invention may be autologous cells derived from a subject or heterologous cells derived from a different subject of the same species. The mesenchymal stem cells are preferably heterologous cells.

The term "ROR1-positive" refers to the expression of ROR1 gene by mesenchymal stem cells, the expression of ROR1 protein, or both. The presence or absence of expression of ROR1 gene or the presence or absence of expression of ROR1 protein in mesenchymal stem cells can be confirmed by a routine method known among persons with ordinary skill in the art. For example, expression of ROR1 gene can be confirmed by isolating total RNA from the cells in accordance with routine methods, synthesizing cDNA, and analyzing expression of ROR1 mRNA by real-time PCR using ROR1 primers. In addition, expression of ROR1 protein on the cell surface can be confirmed by FACS analysis using antibody that specifically binds to ROR1 protein. At that time, an antibody of the same isotype as the aforementioned antibody is used as a negative control. ROR1 is a transmembrane receptor molecule having tyrosine kinase activity that controls neurite outgrowth in the central nervous system. ROR1 is a type I membrane protein that is a member of the ROR subfamily of cell surface receptors. Research is proceeding on ROR1 as a molecule that is involved in metastasis of cancer cells. In addition, ROR1 has recently been determined to be expressed on ovarian cancer stem cells, suggesting the possibility that ROR1 is involved in the infiltration of tissue by cancer. Moreover, ROR1/2 has been determined to function as receptor of Wnt5, which is responsible for non-canonical signaling, suggesting the possibility that this inhibits canonical pathways by vying for Fzd. One example of the effect of increased expression of ROR1 in the mesenchymal stem cell population of the present invention, or an increase in the ratio of ROR1-positive cells, is activation of non-canonical pathways, or in other words, improvement of bone differentiation capacity via inhibition of canonical pathways.

In addition to being characterized by being ROR1-positive, the ROR1-positive mesenchymal stem cells of the present invention may also be characterized by growth characteristics (such as population doubling capacity or doubling time from subculturing to senescence), karyotype analysis (such as having a normal karyotype, maternal lineage or neonatal lineage), surface marker expression as determined by flow cytometry (for example, FACS analysis), immunohistochemistry and/or immunocytochemistry (such as by epitope detection), gene expression profiling (by, for example, using a gene chip array, reversed transcription PCR, real-time PCR, conventional PCR or other type of polymerase chain reaction), miRNA expression profiling, protein array, cytokine or other protein secretion (using, for example, plasma coagulation analysis, ELISA or cytokine array), metabolites (metabolomic analysis), or other methods known in the art. The ROR1-positive mesenchymal stem cells of the present invention have, for example, the characteristics indicated below.

(Surface Marker Expression)

The ROR1-positive mesenchymal stem cells of the present invention express CD29, CD73, CD90, CD105 and CD166 as indicators of undifferentiation.

(Gene Expression)

The ROR1-positive mesenchymal stem cells of the present invention may also be characterized by the presence or absence of the expression of other genes in addition to ROR1 gene. Examples of genes expressed by the ROR1-positive mesenchymal stem cells of the present invention include MT1X, NID2, CPA4, DKK1, ANKRD1, TIMP3, MMP1, osteoprotegerin (TNFRSF11B), IGFBP5 and SLC14A1. Additional examples include superoxide dismutase 2, mitochondrial (SOD2), glutaredoxin (GLRX), heme oxygenase (decycling)-1 (HMOX-1), collagen type IV, alpha (COLA4A), fibronectin 1 and microfibrillar-associated protein 5 (MFAP5), chemokine (C—C motif) ligand 2 (CCL2), chemokine (C—C motif) ligand 7 (CCL7), inhibin beta A (INHBA), interferon-induced protein with tetratricopeptide repeats 1 (IFIT1), interleukin 1, alpha (IL-1α), interleukin 1, beta (IL-1β), endothelin 1 (EDN1), prostaglandin 12 (prostacyclin) synthase (PTGIS), and secreted frizzled-related protein 1 (SFRP1). The ROR1-positive mesenchymal stem cells of the present invention preferably express at least one type of gene selected from the group consisting of MT1X, NID2, CPA4, DKK1, ANKRD1, TIMP3, MMP1, osteoprotegerin (TNFRSF11B), IGFBP5 and SCL14A1. The ROR1-positive mesenchymal stem cells of the present invention more preferably express 2 or more types, 3 or more types, 4 or more types or 5 or more types of the aforementioned genes, even more preferably express 6 or more types, 7 or more types, 8 or more types or 9 or more types, and particularly preferably express all of the aforementioned genes.

In addition, the ROR1-positive mesenchymal stem cells of the present invention may highly express at least one type of gene selected from the group consisting of MT1X, NID2, CPA4, DKK1 and ANKRD1. The ROR1-positive mesenchymal stem cells of the present invention preferably highly express 2 or more types or 3 or more types, more preferably highly express 4 or more types, and even more preferably highly express all of the aforementioned genes. In addition, the ROR1-positive mesenchymal stem cells of the present invention may also highly express superoxide dismutase 2, mitochondrial (SOD2), glutaredoxin (GLRX), heme oxygenase (decycling)-1 (HMOX-1), collagen type IV, alpha (COLA4A), fibronectin 1 or microfibrillar-associated protein 5 (MFAP5) gene. Moreover, the ROR1-positive mesenchymal stem cells of the present invention may also lowly express at least one type of gene selected from the group consisting of TIMP3, MMP1, osteoprotegerin (TNFRSF11B), IGFBP5 and SLC14A1. The ROR1-positive mesenchymal stem cells of the present invention preferably lowly express 2 or more types or 3 or more types, more preferably lowly express 4 or more types, and even more preferably lowly express all of the aforementioned genes. In addition, the ROR1-positive mesenchymal stem cells of the present invention may also lowly express chemokine (C—C motif) ligand 2 (CCL2), chemokine (C—C motif) ligand 7 (CCL7), inhibin beta A (INHBA), interferon-induced protein with tetratricopeptide repeats 1 (IFIT1), interleukin 1, alpha (IL-1α), interleukin 1, beta (IL-1β), endothelin 1 (EDN1), prostaglandin 12 (prostacyclin) synthase (PTGIS) or secreted frizzled-related protein 1 (SFRP1). Here, high expression or low expression of a gene refers to the case in which expression of each gene is increased or expression of each gene is decreased in comparison with conventional ROR1-positive mesenchymal stem cells. More specifically, for example, in the case of using UC-MSC (Umbilical Cord-derived Mesenchymal Stem Cell Wharton's Jelly (HMSC-WJ), FC-0020) available from Lifeline Corp. as umbilical cord-derived mesenchymal stem cells, gene expression can be compared with the expression intensity of each gene in the case of having cultured in the recommended medium of Lifeline Corp.

Furthermore, expression of each gene at this time can be measured by a method known among persons with ordinary skill in the art. For example, the expression of each gene can be analyzed by preparing mRNA from the cells in accordance with routine methods and carrying out RT-PCR on the gene for which the presence or absence and degree of expression is desired to be confirmed.

MT1X is cysteine-rich, low molecular weight protein (molecular weight: 500 Da to 14,000 Da) that is localized in the membranes of Golgi bodies. Although details of the function of MT1X are unknown, the possibility has been suggested that it is involved in the defense mechanism against oxidative stress by functioning as an anti-oxidative protein. In addition, MT1X is also said to be a protein that serves as an indicator of cell undifferentiation. The effect of ROR1-positive mesenchymal stem cells of the present invention expressing MTX is that the cells acquire oxidative stress tolerance, which is preferable in that they are more damage-resistant cells when used for treating diseases.

NID2 binds to laminin γ1 chain and is a protein involved in the formation and maintenance of the basal membrane by linking laminin to type IV collagen. NID2 is expressed in the basal membranes of nearly all central nervous system tissue. One possible effect of the ROR1-positive mesenchymal stem cells of the present invention expressing NID2 is thought to be improvement of the capacity to differentiate into muscle cells (and particularly, skeletal muscle and cardiac muscle cells).

CPA4 is one of the proteases that cleave the C-terminal amino acid of proteins. In addition, CPA4 is a protein also known as a prostate cancer marker, and its expression is known to increase in proportion to the malignancy of cancer. Since expression of CPA4 tends to increase in actively growing, highly undifferentiated cells, expression of CPA4 by the ROR1-positive mesenchymal stem cells of the present invention can be said to suggest that the ROR1-positive mesenchymal stem cells of the present invention demonstrate high levels of undifferentiation and growth.

ANKRD1 is a protein expressed not only by mesenchymal stem cells, but also by cardiac myocytes, smooth muscle cells, fibroblasts and hepatic stellate cells, and is a transcription factor that acts in conjunction with the differentiation process and stress. This gene has also been determined to be involved in numerous heart diseases. In addition, it is known that the expression of ANKRD1 increase in fibroblasts present during the wound healing process and hepatic stellate cells during liver disorders and healing of wounds is delayed in ANKRD1-deleted mice (Susan E. Samaras, et al, The American Journal of Pathology, Vol. 185, No. 1, January 2015; and, Inga Mannaerts, et al, Journal of Hepatology 2015). In addition, it is also a nuclear factor that controls expression of MMP10, MMP13 and other extracellular matrix degrading enzymes (Karinna Almodovar-Garcia, et al, MCB 2014). Accordingly, possible effects of expression of ANKRD1 by the ROR1-positive mesenchymal stem cells of the present invention are thought to include the potentiation for improving the capacity to differentiate into cardiac myocytes, enhancing wound healing effects and involvement in remodeling of the extracellular matrix of fibrotic tissue.

DKK1 is a protein that functions as a Wnt signaling inhibitor and is thought to be involved in inhibition of canonical pathways. Consequently, it improves bone differentiation capacity by acting to promote bone differentiation. Expression of DKK1 is known to decrease in osteoporosis. On the other hand, it is thought to have a beneficial effect on maintaining undifferentiation and growth of cells, and is also known to contribute to fetal development.

TIMP3 (Tissue Inhibitor of Metalloproteinase 3) inhibits activation of MMP1, MMP2, MMP3, MMP9 and MMP13. Moreover, since MMP3 is involved in the activation of numerous other MMP, TIMP3 functions as a wide-ranging MMP inhibitory factor. In addition, TIMP3 is also known to inhibit vascularization by inhibiting binding of VEGF to VEGFR2 as well as function as an apoptosis promoting signal.

MMP1 (matrix metalloproteinase 1) is a protein that degrades type I, type II, type III and type IV collagen. Since it is mainly targeted at ECM, it is known to function during cell division and chemotaxis. Expression of MMP1 is also known to increase in response to an inflammatory reaction, and is involved in tissue destruction and remodeling during inflammation.

Osteoprotegerin (TNFRSF11B) is a decoy receptor of osteoclast differentiation factor (RANKL) and inhibits activation of NF-κB signaling mediated by RANK. It is produced by osteoblasts, fibroblasts and hepatocytes, and inhibits differentiation of osteoclast progenitor cells into osteoclasts. Local administration of osteoprotegerin has been reported to promote osteogenesis, while conversely to induce osteoporosis as a result of knockdown.

IGFBP-5 is a protein that binds insulin-like growth factor and nearly all IGF is present in a form bound to IGFBP. One example of the function of IGFBP is enhancement of IGF signaling. In addition, IGFBP-5 is also known to inhibit TNFα signaling as a result of promoting gene expression by TNFR1 while also acting antagonistically on TNFR1 protein. In addition, IGFBP-5 has been reported to promote cell adhesion and increase cell viability in breast cancer cells as well as inhibit chemotaxis.

SLC14A1 is a urea transporter that is highly expressed in the kidneys and controls intracellular urea concentration. It has also been shown to be expressed in mesenchymal stem cells and expression has been reported to decrease during cartilage differentiation in particular.

SOD2 is an ROS (active enzyme) eliminating enzyme, GLRX is an oxidoreductase, HMOX-1 is an anti-oxidative enzyme, COLA4A is a protein that composes the basal membrane, and fibronectin 1 and MFAP5 are proteins involved in matrix formation. In addition, CCL2, CCL7, INHBA, IFIT1, IL-1α, IL-1β, EDN1 and PTGIS are proteins relating to inflammation, while SFRP1 is a protein involved in inhibition of Wnt signaling.

(Microrna Expression)

The ROR1-positive mesenchymal stem cells of the present invention may also be further characterized by the presence or absence of expression of miRNA. Examples of miRNA expressed by the ROR1-positive mesenchymal stem cells of the present invention include hsa-miR-145-5p, hsa-miR-181a-5p, hsa-miR-29b-3p, hsa-miR-34a-5p, hsa-miR-199b-5p, hsa-miR-503-5p, hsa-let-7e-5p, hsa-miR-132-3p, hsa-miR-196a-5p, hsa-miR-324-3p, hsa-miR-328-3p, hsa-miR-382-5p and hsa-let-7d-5p. The ROR1-positive mesenchymal stem cells of the present invention preferably express at least one type of microRNA selected from the group consisting of hsa-miR-145-5p, hsa-miR-181a-5p, hsa-miR-29b-3p, hsa-miR-34a-5p, hsa-miR-199b-5p, hsa-miR-503-5p, hsa-let-7e-5p, hsa-miR-132-3p, hsa-miR-196a-5p, hsa-miR-324-3p, hsa-miR-328-3p, hsa-miR-382-5p and hsa-let-7d-5p. The ROR1-positive mesenchymal stem cells of the present invention more preferably express 2 or more types, 3 or more types, 4 or more types, 5 or more types or 6 or more types of the aforementioned microRNA, even more preferably express 7 or more types, 8 or more types, 9 or more types, 10 or more types, 11 or more types or 12 or more types, and particularly preferably express all of the aforementioned microRNA.

In addition, at least one type of microRNA selected from the group consisting of hsa-miR-145-5p, hsa-miR-181a-5p, hsa-miR-29b-3p, hsa-miR-34a-5p, hsa-miR-199b-5p and hsa-miR-503-5p preferably tends to be lowly expressed, and at least one type of microRNA selected from the group consisting of hsa-let-7e-5p, hsa-miR-132-3p, hsa-miR-196a-5p, hsa-miR-324-3p, hsa-miR-328-3p, hsa-miR-382-5p and hsa-let-7d-5p preferably tends to be highly expressed. Here, low expression of microRNA refers to a low level of expression in comparison with ROR1-negative mesenchymal stem cells. Conversely, high expression of microRNA refers to a high level of expression in comparison with ROR1-negative mesenchymal stem cells. More specifically, in the case of using UC-MSC (Umbilical Cord-derived Mesenchymal Stem Cell Wharton's Jelly (HMSC-WJ), FC-0020) available from Lifeline Corp. as umbilical cord-derived mesenchymal stem cells, for example, gene expression can be based on the expression intensity of each microRNA in the case of having cultured in the recommended medium of Lifeline Corp.

Furthermore, the expression of microRNA at this time can be measured in accordance with methods known among persons with ordinary skill in the art. For example, expression of microRNA in cells can be analyzed by preparing mRNA from the cells in accordance with routine methods and carrying out qRT-PCR or using a commercially available microRNA array. Determination of the expression level of microRNA can be carried out by calculating the value (Fold change value) obtained by dividing the expression level of each type of microRNA in cells obtained by culturing in formulated medium by the expression level of each microRNA in cells obtained by culturing in conventional medium or recommended medium.

(Cytokine Secretion)

The ROR1-positive mesenchymal stem cells of the present invention may also be further characterized by the presence or absence of cytokine secretion. Examples of cytokines secreted by the ROR1-positive mesenchymal stem cells of the present invention include decorin, osteoprotegerin and MMP1. The ROR1-positive mesenchymal stem cells of the present invention preferably secrete at least one type of cytokine selected from the group consisting of decorin, osteoprotegerin and MMP1, more preferably secrete at least two types of cytokines, and even more preferably secrete all three types of cytokines.

In addition, the ROR1-positive mesenchymal stem cells of the present invention preferably secrete a large amount of decorin and small amounts of osteoprotegerin and MMP1. Here, determination as to whether the secreted amount of each factor is large or small can be carried out by comparing with the amount of each factor produced (or concentration in culture supernatant) in ROR1-negative mesenchymal stem cells.

Furthermore, the secreted amount of cytokine (or concentration in culture supernatant) can be measured according to a method known among persons with ordinary skill in the art. An example of such a method is ELISA.

Decorin is one of the most commonly known factors of the family of small, leucine-rich proteoglycans. Decorin is expressed ubiquitously in the body and is known to be involved in the aggregation of collagen fibers and the proliferation of cells. Examples of the expected effects of increased secretion of decorin in the ROR1-positive mesenchymal stem cells of the present invention include the effect of repairing tissue at sites of inflammation and tissue damage and the effect of promoting cell growth in tissue.

As was previously described in the section on gene expression, osteoprotegerin (TNFRSF11B) is a decoy receptor of osteoclast differentiation factor (RANKL) that inhibits activation of NF-κB signaling mediated by RANK. It is produced in osteoblasts, fibroblasts and hepatocytes, and inhibits differentiation of osteoclast progenitor cells into osteoclasts. Local administration of osteoprotegerin has been reported to promote osteogenesis, while conversely to induce osteoporosis as a result of knockdown.

As was previously described in the section on gene expression, MMP1 (matrix metalloproteinase 1) is an interstitial collagenase involved in tissue destruction and tissue reconstruction by specifically cleaving the helix sites of type I, type II, type III and type IV collagen. The effect of lower secretion of MMP1 in the ROR-1 positive mesenchymal stem cells of the present invention compared to ROR1- negative cells is expected to be effective in repairing tissues at sites of inflammation and damage.

(Differentiation Directionality)

The ROR1-positive mesenchymal stem cells of the present invention have excellent capacity to differentiate into bone, adipose tissue and cartilage. Each of these differentiation capacities can be determined by culturing a population of the aforementioned mesenchymal stem cells under conditions that induce differentiation known among persons with ordinary skill in the art.

A conventionally used induction method can be used for the method used to induce differentiation to osteocytes, and although there are no particular limitations thereon, differentiation can typically be induced according to a method like that described below. Namely, after having cultured the ROR1-positive mesenchymal stem cells of the present invention for several days, the cells are suspended and seeded in a differentiation culture broth containing FBS or other serum, dexamethasone, β-glycerol phosphate and ascorbic acid-2-phosphate therein. Furthermore, a commercially available osteocyte differentiation medium may also be used for the aforementioned differentiation culture broth. Examples of such commercially available bone differentiation media include Osteolife Complete Osteogenesis Medium (Lifeline Corp., LM-0023) and Mesenchymal Stem Cell Osteogenic Differentiation Medium (Takara Bio Inc., D12109). When culturing to induce bone differentiation, the medium is replaced about 24 to 72 hours after seeding the cells for differentiation culturing, the medium is replaced every 3 to 4 days thereafter, and the cells are cultured for about 2 weeks to 1 month.

A conventionally used induction method can be used for the method used to induce differentiation into adipocytes, and although there no particular limitations thereon, the method typically consists of suspension culturing the cells for several days in a culture broth containing retinoic acid, followed by culturing in a culture broth containing insulin and triiodothyronine (T3). In addition, culture conditions conventionally used for culturing this type of cell can be used, and there are no particular limitations on, for example, the type of medium, contents of the composition, concentration of the composition and incubation temperature. In addition, although a period of not more than 21 days is typically preferable for the incubation period, culturing can be continued for about 30 days to 40 days. More specifically, adipocytes can be induced according to the method described below. Namely, after having cultured the ROR1-positive mesenchymal stem cells of the present invention for several days, the cells are seeded at the recommended cell density as stated in the Kurabo protocol by suspending in adipocyte differentiation medium. Examples of the aforementioned differentiation medium include human mesenchymal stem cell adipocyte differentiation medium such as AdipoLife DfKt-1 (Lifeline Corp., LL-0050), AdipoLife DfKt-2 (Lifeline Corp., LL-0059) or Mesenchymal Stem Cell Adipogenic Differentiation Medium (Takara Bio Inc., D12107). When culturing for differentiation into adipocytes, the medium is replaced about 24 to 72 hours after seeding the cells for differentiation culturing, the medium is replaced every 3 to 4 days thereafter, and the cells are cultured for about 2 weeks to 1 month.

A conventionally used induction method can be used for the method used to induce differentiation into chondrocytes, and although there are no particular limitations thereon, the method typically consists of mixing the ROR1-positive mesenchymal stem cells of the present invention with collagen gel and the like to form a gel followed by culturing in DMEM medium after adding differentiation culture broth thereto containing dexamethasone, ascorbic acid-2-phosphate, sodium pyruvate, transforming growth factor β3 (TGF-β3) and ITS Plus Premix (mixture of insulin, transferrin and selenite). The cells are cultured for about 3 weeks while replacing the medium about two to three times a week. More specifically, chondrocytes can be induced according to the method described below. Namely, after having cultured the ROR1-positive mesenchymal stem cells of the present invention for several days, the cells are seeded using the micro mass method at the recommended cell density as stated in the Kurabo protocol by suspending in chondrocyte differentiation medium. Examples of the aforementioned chondrocyte differentiation medium include ChondroLife Complete Chondrogenesis Medium (Lifeline Corp., LM-0023) and Mesenchymal Stem Cell Chondrogenic Differentiation Medium w/o Inducers (Takara Bio Inc., D12110). The medium is replaced every 3 to 4 days thereafter, and the cells are cultured for about 2 weeks to 1 month.

Cells obtained according to the aforementioned differentiation induction methods can be confirmed for the type of differentiated cells by using a biochemical approach or morphological observation. For example, the type of differentiated cells can be identified by various confirmation methods such as observing the cells with a microscope, various cell staining methods, northern blotting using hybridization or RT-PCR.

Although adipocytes, osteocytes and chondrocytes are difficult to identify based on cell morphology, the presence of adipocytes can be confirmed by staining for intracellular lipids (which can be stained red with Oil Red 0 stain, for example). In addition, the presence of osteocytes can be confirmed by staining the cells with Alizarin red. In addition, the presence of chondrocytes can be confirmed by staining with Alcian blue, Safranin O or Toluidine blue.

Although the ROR1-positive mesenchymal stem cells of the present invention have the capacity to differentiate into adipocytes, osteocytes and chondrocytes, the capacity to differentiate into adipocytes in particular is remarkably improved in comparison with mesenchymal stem cell populations cultured with recommended medium.

(Resistance to Oxidative Stress)

The ROR1-positive mesenchymal stem cells of the present invention are less susceptible to damage by oxidative stress caused by rotenone, $H_2O_2$, etc. in comparison with ROR1-negative mesenchymal stem cells. Namely, when ROR1-positive mesenchymal stem cells are compared with ROR1-negative mesenchymal stem cells for cell viability (%) after treating with equal concentrations of rotenone and $H_2O_2$, in contrast to the ROR1-negative mesenchymal stem cells demonstrating a considerable concentration-dependent decrease in viability, the ROR1-positive mesenchymal stem cells of the present invention are inhibited decreases in viability, and some cells, may demonstrate viability approaching 100%.

(Migratory Capacity and Inhibition of Cancer Cell Migration)

The ROR1-positive mesenchymal stem cells of the present invention demonstrate superior migratory capacity in comparison with ROR1-negative mesenchymal stem cells. In addition, a culture supernatant of the ROR1-positive mesenchymal stem cells of the present invention demonstrate a high level of inhibitory activity on the migration of cancer cells in comparison with a culture supernatant of ROR1-negative mesenchymal stem cells. Namely, the ROR1-positive mesenchymal stem cells of the present invention are able to suitably migrate to a site of action due to the excellent migratory ability thereof, and furthermore at the site of action, the ROR1-positive mesenchymal stem cells or factors produced by them are thought to be able to inhibit infiltration and metastasis of cancer cells, for example, by inhibiting migration of cancer cells and the like.

(Mitochondrial Transfer Capacity)

In the present invention, "mitochondrial transfer capacity" refers to the ability of cells to allow mitochondria to migrate to other cells or the ability of mitochondria per se to migrate to other cells, and in the case of co-culturing a plurality of cells, the degree of that migratory capacity is expressed as a ratio (%) of the number of cells that have undergone mitochondrial transfer to the total number of cells on the receiving side of that mitochondrial transfer. Furthermore, in addition to mitochondria per se, examples of transferred mitochondria referred to here include mitochondrial genes (DNA, RNA), various proteins, and complexes of these components with other proteins or other organs such as endoplasmic reticulum contained in mitochondria. In the case specific cells demonstrate superior mitochondrial transfer capacity, these cells can be expected to demonstrate therapeutic effects on various diseases as well as recovery effects on symptoms accompanying aging and the like.

As a result of having superior mitochondria transfer capacity and transferring mitochondria to cells having impaired mitochondrial function or reduced mitochondrial activity, the ROR1-positive mesenchymal stem cells of the present invention demonstrate superior effects against symptoms associated with each diseases and aging or stress and the like. Although there are no particular limitations thereon, examples of cells (cells on recipient side), capable of accepting mitochondrial transfer from the ROR1-positive mesenchymal stem cells of the present invention include cardiac myocytes, alveolar epithelial cells, renal tubule cells, astrocytes, bronchial smooth muscle cells, vascular smooth muscle cells, vascular endothelial cells, immune cells (such as macrophages), epidermal stem cells, dermal fibroblasts and corneoconjunctival epithelial stem cells, with preferable examples of the aforementioned cells including cardiac myocytes, dermal fibroblasts and bronchial smooth muscle cells, and these cells in which the function thereof has been depressed due to disease, aging or stress and the like are particularly preferable.

[Preparation of ROR1-Positive Mesenchymal Stem Cells]

Although there are no particular limitations on the method used to prepare the ROR1-positive mesenchymal stem cells, the cells can be prepared according to, for example, the method indicated below. Namely, mesenchymal stem cells are isolated from umbilical cord, adipose tissue or bone marrow and the like and cultured in accordance with a method known among persons with ordinary skill in the art followed by acquiring ROR1-positive cells by isolating with a cell sorter or magnetic beads and the like using anti-ROR1 antibody that specifically binds with ROR1. In addition, ROR1-positive mesenchymal stem cells can also be acquired by inducing expression of ROR1 in mesenchymal stem cells by culturing using a medium to be subsequently described. Preferably 70% or more of the cell population obtained by this induction is ROR1-positive, more preferably 80% or more is ROR1-positive, even more preferably 90% or more is ROR1-positive, and the cell population particularly preferably consists of a substantially homogeneous population of ROR1-positive cells. The following provides a detailed explanation of a method for preparing ROR1-positive mesenchymal stem cells.

A method like that indicated below, for example, can be used to prepare ROR1-positive mesenchymal stem cells in the present invention. Namely, mesenchymal stem cells can be acquired and cultured by a method that includes the steps of (A) a step for treating tissue containing mesenchymal stem cells with enzyme, (B) a step for carrying out adhesion culturing by suspending the cell suspension obtained according to the aforementioned treatment in a suitable culture medium, (C) a step for removing suspended cells, and (D) a step for culturing the mesenchymal stem cells. The following provides a detailed explanation of each step.

In step (A) for treating tissue containing mesenchymal stem cells with enzyme, the tissue containing mesenchymal stem cells such as umbilical cord is washed by agitating and precipitating using physiological saline (such as phosphate-buffer saline (PBS)), for example. Contaminants contained in the aforementioned tissue can be removed from the tissue by this procedure. Since the remaining cells are present in the form of aggregates of various sizes, the washed cell aggregates are preferably treated with enzyme that weakens or destroys the bonds between cells (such as collagenase, dispase or trypsin) in order to dissociate the cells while minimizing damage thereto. Although the amount of enzyme used and the duration of enzyme treatment vary dependent upon the conditions used, treatment can be carried out within the scope of common general technical knowledge in the art. Although the cell aggregates can also be broken up with other treatment methods such as mechanical agitation, ultrasonic energy or thermal energy either in place of or in combination with this enzyme treatment, treating the cells with enzyme alone is preferable in order to minimize cell damage. In the case of using an enzyme, the enzyme is preferably deactivated using medium and the like following enzyme treatment in order to minimize any harmful action on the cells.

The cell suspension obtained according to the aforementioned process contain contains a slurry or suspension of aggregated cells and various contaminant cells such as erythrocytes, smooth muscle cells, endothelial cells or fibroblasts. Thus, although the aggregated cells and these contaminant cells may be subsequently separated and removed, since removal is possible by a suspended cell removal step to be subsequently described, this separation and removal may be omitted. In the case of separating and removing contaminant cells, separation and removal can be achieved by centrifugation that forcibly separates the cells into supernatant and precipitate. The resulting precipitate containing contaminant cells is suspended in a suitable solvent. Although suspended cells may contain erythrocytes, since erythrocytes are excluded by selecting the erythrocytes by adhering to a solid surface to be subsequently described, a lysing step is not necessarily required. A method known in the art such as incubation in a hypertonic medium or hypotonic medium obtained by lysing with ammonium chloride can be used to selectively lyse erythrocytes. After lysing, the lysed fragments may be separated from the desired cells by, for example, filtration, centrifugal sedimentation or density fractionation.

Next, in step (B) for carrying out adhesion culturing by suspending the cell suspension obtained according to the aforementioned enzyme treatment in a suitable culture medium, the suspended cells may be washed once or multiple times continuously, centrifuged, and re-suspended in a culture medium, in order to increase the purity of mesenchymal stem cells. In addition, the cells may be separated on the basis of a cell surface marker profile or on the basis of cell size and granularity. In this step, only those cells expressing ROR1 protein may be selectively separated by a cell sorter or an immunochemical technique using magnetic beads and the like.

There are no particular limitations on the medium used for re-suspending the cells provided that it enables mesenchymal stem cells to be cultured, and for example, it can be prepared by adding serum and/or a serum substitute to basal medium for culturing animal cells. In addition, commercially available media may also be used as medium suitable for culturing mesenchymal stem cells. Furthermore, in the present invention, medium not containing biological raw materials (such as serum-free medium) as possible is preferably used in order to allow the mesenchymal stem cells or culture supernatant thereof to be used to treat animal (including human) diseases. Media not containing components derived from different species (such as Xeno-Free medium) is particularly preferable.

The composition of the aforementioned basal medium can be suitably selected according to the type of cells to be cultured. Examples thereof include minimum essential medium (MEM) such as Eagle's medium, Dulbecco's modified Eagle's medium (DMEM), minimum essential medium α(MEM-α), mesenchymal stem cell basal medium (MSCBM), Ham's F-12 and F-10 medium, DMEM/F12 medium, William's medium E, RPMI-1640 medium, MCDB medium, 199 medium, Fisher's medium, Iscove's modified Dulbecco's medium (IMDM) and McCoy's modified medium.

Examples of serum include, but are not limited to, human serum, fetal bovine serum (FBS), bovine serum, bovine calf serum, goat serum, horse serum, pig serum, sheep serum, rabbit serum and rat serum. In the case of using serum, serum may be added to basal medium at 0.5% to 15% and preferably at 5% to 10%.

Examples of serum substitutes added to the basal medium include albumin, transferrin, fatty acids, insulin, sodium selenite, collagen precursor, trace elements, 2-mercaptoethanol and 3'-thioglycerol.

Examples of substances added to the aforementioned basal medium include, but are not limited to, amino acids, inorganic salts, vitamins, growth factors, antibiotics, trace metals, stem cell differentiation inducers, antioxidants, carbon sources, salts, sugars, sugar precursors, plant-derived hydrolysates, surfactants, ammonia, lipids, hormones, buffers, indicators, nucleosides, nucleotides, butyric acid, organic matter, DMSO, plant-derived products, gene induction agents, intracellular pH adjusters, betaine, osmoprotectants and minerals. There are no particular limitations on the concentrations at which these substances are used, and can be used at concentrations used in ordinary mammalian cell media.

Examples of the aforementioned amino acids include glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and L-valine.

Examples of the aforementioned inorganic salts include calcium chloride, copper sulfate, iron (II) nitrate, iron sulfate, magnesium chloride, magnesium sulfate, potassium chloride, sodium bicarbonate, sodium chloride, disodium hydrogen phosphate and sodium dihydrogen phosphate.

Examples of the aforementioned vitamins include choline, vitamin A, vitamin B1, vitamin B2, vitamin B3, vitamin B4, vitamin B5, vitamin B6, vitamin B7, vitamin B12, vitamin B13, vitamin B15, vitamin B17, vitamin Bh, vitamin Bt, vitamin Bx, vitamin C, vitamin D, vitamin E, vitamin F, vitamin K, vitamin M and vitamin P.

In addition, specific examples of substances able to added to the basal medium include growth factors such as basic fibroblast growth factor (bFGF), endothelial growth factor (EGF), platelet-derived growth factor (PDGF), epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte-colony stimulating factor (G-CSF), granulocyte-macrophage colony stimulating factor (GM-CSF), erythropoietin (EPO), thrombopoietin (TPO) or hepatocyte growth factor (HGF), antibiotics such as penicillin, streptomycin, neomycin sulfate, amphotericin B, blastocydine, chloramphenicol, amoxicillin, bacitracin, bleomycin, cephalosporin, chlortetracycline, zeocin or puromycin, carbon sources such as glucose, galactose, fructose or sucrose, trace metals such as magnesium, iron, zinc, calcium, potassium, sodium, copper, selenium, cobalt, tin, molybdenum, nickel or silicon, stem cell differentiation inducers such as β-glycerophosphoric acid, dexamethasone, rosiglitazone, isobutyl methylxanthine or 5-azacytidine, antioxidants such as 2-mercaptoethanol, catalase, superoxide dismutase or N-acetylcysteine, adenosine-5'-monophosphate, corticosterone, ethanolamine, insulin, reduced glutathione, lipoic acid, melatonin, hypoxanthine, phenol red, progesterone, putrescine, pyruvic acid, thymidine, triiodothyronine, transferrin and lactoferrin.

Examples of serum-free media preferable for the mesenchymal stem cells of the present invention include commercially available, serum-free media. Examples thereof include pre-prepared media for mesenchymal stem cells available from PromoCell GmbH, Lonza Group Ltd., Biological Industries Inc., Veritas Corp., R&D Systems Inc., Corning Inc. and Rohto Pharmaceutical Co., Ltd.

Continuing, the mesenchymal stem cells are cultured at a suitable cell density and under suitable culturing conditions using a suitable medium as described above on a solid surface such as a culture vessel without differentiating the mesenchymal stem cells. There are no particular limitations on the shape of the culture vessel having a solid surface and a Petri dish or flask is used preferably. There are no particular limitations on the culturing conditions of the mesenchymal stem cells of the present invention provided they are suitable for each type of mesenchymal stem cell, and a method similar to that of the prior art is used. Normally, culturing is carried out at a temperature of 30° C. to 37° C. in an environment containing 2% to 7% $CO_2$ and 5% to 21% $O_2$. In addition, there are also no particular limitations on the timing and method used to subculture the mesenchymal stem cells provided they are suitable for each type of cell, and those similar to the prior art can be used while monitoring the status of the cells.

In step (C) for removing suspended cells, suspended cells and cell fragments not adhered to the solid surface of the culture vessel are removed followed by washing the adhered cells using physiological saline (such as phosphate-buffered saline (PBS)). In the present invention, cells ultimately remaining in an adhered state to the solid surface of the culture vessel can be selected for use as a cell population of mesenchymal stem cells.

Next, step (D) for culturing the mesenchymal stem cells is carried out. There are no particular limitations on the culturing method provided it is suitable for each type of cell. Normally, culturing is carried out at a temperature of 30° C. to 37° C. in an environment containing 2% to 7% $CO_2$ and 5% to 21% $O_2$. In addition, there are also no particular limitations on the timing and method used to subculture the mesenchymal stem cells provided they are suitable for each type of cell, and those similar to the prior art can be used while monitoring the status of the mesenchymal stem cells. The same medium as that used in step (B) can be used for the medium used for culturing. Furthermore, culturing may be carried out using serum-free medium throughout the entire cell incubation period.

ROR1-positive mesenchymal stem cells can be acquired by selectively separating only those cells expressing ROR1 protein from the mesenchymal stem cells obtained according to the culturing of step (D) by a cell sorter or an immunochemical technique using magnetic beads and the like.

Furthermore, in the steps following the aforementioned step (B), ROR1 expression can be induced in the mesenchymal stem cells and ROR1-positive mesenchymal stem cells can be acquired efficiently by using, for example, the media described below.

[Induction of ROR1 Expression (Specific Media for Mesenchymal Stem Cells)]

Examples of specific media used to induce expression of ROR1 and efficiently acquire ROR1-positive mesenchymal stem cells (to also be referred to as the "formulated medium") include a medium containing at least two types of components selected from the group consisting of PTEN inhibitors, p53 inhibitors, p38 inhibitors, Wnt signaling activators and ROCK inhibitors, and basal medium for culturing animal cells. As a result of containing these components, the formulated medium is able to induce or promote expression of ROR1 in mesenchymal stem cells as well as culture the mesenchymal stem cells while maintaining in an undifferentiated state over a long period of time. In addition, the formulated medium allows mesenchymal stem cells to grow efficiently while maintaining favorable cell status over a long period of time. Moreover, the formulated medium preferably further contains at least one type of component selected from the group consisting of growth factors and steroid compounds. The following provides a detailed explanation of the components contained in the formulated medium.

(PTEN Inhibitors)

In the present invention, a PTEN inhibitor refers to phosphatase and tensin homolog deleted from chromosome 10) gene or all substances having a function that inhibits the action of PTEN protein. PTEN gene is located on chromosome 10q23.3 and has been identified as a tumor suppressor. PTEN protein is expressed widely in whole body cells, and is known to be an enzyme that catalyzes the dephosphorylation reaction of the inositol phospholipid, phosphatidylinositol 3,4,5-triphosphate (PIP3)). PIP3 is synthesized in cells by PI3 kinase (PI3K) and induces activation of protein kinase B (PKB)/AKT. PTEN is responsible for the dephosphorylation of this PIP3, and is considered to demonstrate action that converts PIP3 to phosphatidylinositol 4,5-bisphosphate (PIP2)). Thus, PTEN negatively controls the PI3K/AKT signal transduction system. When the activity of PTEN is inhibited, PIP3 accumulates in cells resulting in activation of the PI3K/AKT signal transduction system.

Examples of PTEN inhibitors in the present invention include pV (phenbig) (dipotassium bisperoxo(phenylbiguanide) oxovanadate), bpV (HOPic) (dipotassium bisperoxo (5-hydroxypyridine-2-carboxyl) oxovanadate), and VO-OHPic trihydrate ((OC-6-45) Aqua (3-hydroxy-2-piperidine carboxylate-kapaN1, kapa02) [3-(hydroxy-kapaO)-2-piperidine carboxylate (2-)-kapa02] oxovanadate (1-), hydrogen trihydrate). These can be used alone or two or more types can be used in combination.

From the viewpoint of the effects of the present invention, the concentration of PTEN inhibitor in the formulated medium is preferably 10 nM to 10 μM, more preferably 50 nM to 1 μM, even more preferably 100 nM to 750 nM, and particularly preferably 250 nM to 750 nM.

(p53 Inhibitors)

In the present invention, a p53 inhibitor refers to all substances having a function that inhibits the action of p53 gene or p53 protein. p53 protein is located on chromosome 17p13.1 and is known to be a tumor suppressor. p53 protein acts as a transcription factor and demonstrates diverse physiological activity.

Examples of p53 inhibitors in the present invention include sodium orthovanadate, pifithrin-α and MDM2 protein. These can be used alone or two or more types can be used in combination.

From the viewpoint of the effects of the present invention, the concentration of p53 inhibitor in the formulated medium is preferably 100 nM to 1 mM, more preferably 500 nM to 500 μM, and even more preferably 1 μM to 100 μM.

(p38 Inhibitors)

In the present invention, a p38 inhibitor refers to all substances having a function that inhibits the action of p38 gene or p38 protein. p38 is serine/threonine kinase in the form of a mitogen-activated protein kinase (MAP kinase). MAP kinase has been determined to be involved in signaling molecules that transmit external stimuli, cell growth, cell differentiation, gene expression and apoptosis.

Examples of p38 inhibitors in the present invention include SB203580 (methyl [4-[4-(4-fluorophenyl)-5-(4-pyridinyl)-1H-imidazol-2-yl]phenyl]sulfoxide), SB202190 (4-[4-(4-fluorophenyl)-5-(4-pyridinyl)-1H-imidazol-2-yl] phenol), BIRB796 (Doramapimod: 1-[5-tert-butyl-2-(4-methylphenyl)-2H-pyrazole-3-yl]-3-[4-(2-morpholinoethoxy)-1-naphthyl] urea), LY2228820 (5-[2-(1,1-dimethylethyl)-5-(4-fluorophenyl)-1H-imidazol-4-yl]-3-(2, 2-dimethylpropyl)-3H-i midazo[4,5-b]pyridine-2-amine dimethanesulfonate), VX-702 (2-(2,4-difluorophenyl)-6-[(2,6-difluorophenyl) (aminocarbonyl)amino]pyridine-3-carboxamide), PH-797804 (N,4-dimethyl-3-[3-bromo-4-[(2, 4-difluorobenzyl)oxy]-6-methyl-2-oxo-1,2-dihydropyridine-1-yl]benzamide), TAK-715 (N-[4-[2-ethyl-4-(3-methylphenyl)thiazole-5-yl]-2-pyridyl]benzamide), VX-745 (5-(2,6-dichlorophenyl)-2-[(2,4-difluorophenyl) thio]-6H-pyrimido[1,6-b]pyridazin-6-one), and Skepinone-L ((2R)-3-[8-[(2,4-difluorophenyl)amino]-5-oxo-5H-dibenzo[a,d]cycloheptene-3-yloxy]-1,2-pro panediol). These can be used alone or two or more types can be used in combination.

From the viewpoint of the effects of the present invention, the concentration of p38 inhibitor in the formulated medium is preferably 1 nM to 1 μM, more preferably 10 nM to 500 nM, and even more preferably 50 nM to 250 nM.

(Wnt Signaling Activators)

In the present invention, a Wnt signaling activator refers to all substances that activate Wnt signaling. Wnt is a secretory intercellular signal transduction protein that is involved in intracellular signal transduction. This signal transduction pathway controls functions such as cell growth and differentiation, cell motility, or body axis formation or organogenesis during early embryonic development. The Wnt signaling pathway includes several intracellular signal transduction mechanisms separately activated by the action of Wnt on cells. The Wnt signaling pathway is known to consist of a β-catenin pathway that controls gene expression mediated by β-catenin, a planar cell polarity (PCP) pathway that controls planar cell polarity, and a $Ca^{2+}$ pathway that promotes intracellular mobilization of $Ca^{2+}$. In the present description, a Wnt signaling activator may activate any of these pathways.

Wnt signaling activators in the present invention include catenin-dependent activators in the manner of Wnt-3 and catenin-independent activators in the manner of Wnt-5. In addition, lithium chloride (LiCl) or complement molecule Clq can also be used. These can be used alone or two more types can be used in combination.

From the viewpoint of the effects of the present invention, the concentration of Wnt signaling activator in the formulated medium is preferably 1 μM to 10 mM, more preferably 10 μM to 10 mM, even more preferably 100 μM to 1 mM, and particularly preferably 100 μM to 500 μM.

(Rock Inhibitors)

In the present invention, a ROCK inhibitor refers to all substances that inhibit the action of Rho kinase (ROCK). Rho kinase (ROCK) is a serine-threonine protein phosphatase that has been identified as a target protein of Rho, which is a low molecular weight GTP-binding protein. Rho kinase is involved in physiological functions such as muscle contraction, cell growth, chemotaxis and induction of the expression of other genes.

Examples of ROCK inhibitors in the present invention include Y-27632 [(R)-(+)-trans-N-(4-pyridyl)-4-(1-amino-ethyl)-cyclohexanecarboxamide.2HCl.$H_2O$], K-155 (ripasudil hydrochloride hydrate), and fasudil hydrochloride (HA1077: 1-(5-isoquinolinesulfonyl)homopiperazine hydrochloride).

From the viewpoint of the effects of the present invention, the concentration of ROCK inhibitor in the formulated medium is preferably 1 nM to 10 μM, more preferably 10 nM to 1 μM and even more preferably 50 nM to 500 nM.

Although the formulated medium contains at least two components selected from the group consisting of the aforementioned PTEN inhibitors, p53 inhibitors, p38 inhibitors, Wnt signaling activators and ROCK inhibitors, from the viewpoint of the effects of the present invention, the formulated medium preferably contains three types of these components, more preferably contains four types of these components, and even more preferably contains all five types of these components.

(Growth Factors)

Any growth factor known among persons with ordinary skill in the art can be used as growth factor in the present invention. Typical examples thereof are not limited to transforming growth factor (TGF) or epidermal growth factor (EGF), but also include insulin-like growth factor (IGF), nerve growth factor (NGF), brain-derived neurotrophic factor (BDNF), vascular endothelial growth factor (VEGF), granulocyte-colony stimulating factor (G-CSF), granulocyte-macrophage colony stimulating factor (GM-CSF), platelet-derived growth factor (PDGF), erythropoietin (EPO), thrombopoietin (TPO), basic fibroblast growth factor (bFGF or FGF2) and hepatocyte growth factor (HGF). Moreover, additional examples include albumin, transferrin, lactoferrin and fetuin. These can be used alone or two or more types can be used in combination.

A suitable concentration according to the type of growth factor is used for the concentration of growth factor in the formulated medium. In general, from the viewpoint of the effects of the invention, the concentration of growth factor is preferably 1 nM to 100 mM and more preferably 10 nM to 10 mM.

(Steroid Compounds)

Any steroid compound known among persons with ordinary skill in the art can be used as a steroid compound in the formulated medium. Typical examples of steroid compounds that can be used include, but are not limited to, steroid hormones such as estradiol, progesterone, testosterone, cortisone, cortisol or hydrocortisone. These can be used alone or two or more types can be used in combination.

A suitable concentration according to the type of steroid compound can be used for the concentration of steroid compound in the formulated medium. In general, from the viewpoint of the effects of the present invention, the concentration is preferably 0.1 nM to 1 mM, more preferably 1 nM to 100 μM, and even more preferably 10 nM to 1 μM.

(Basal Medium for Culturing Animal Cells)

The basal medium for culturing animal cells in the present invention refers to medium containing components such as a carbon source, nitrogen source and inorganic salt essential for culturing animal cells. Here, animal cells refer to mammalian cells, and particularly human cells. The basal medium for culturing animal cells in the present invention preferably does not contain biological raw materials (such as serum-free medium) as possible when considering the potential for use of the cultured cells or culture supernatant thereof in the treatment of animal (including human) diseases. The basal medium for culturing animal cells may incorporate trace effective amounts of micronutrient promoting substances or precursors thereof as necessary. Media for culturing animal cells known among persons with ordinary skill in the art can be used for this medium for culturing animal cells. Specific examples thereof include minimum essential medium (MEM) such as Eagle's medium, Dulbecco's modified Eagle's medium (DMEM), minimum essential medium α(MEM-α), mesenchymal stem cell basal medium (MSCBM), Ham's F-12 and F-10 medium, DMEM/F12 medium, William's medium E, RPMI-1640 medium, MCDB medium, 199 medium, Fisher's medium, Iscove's modified Dulbecco's medium (IMDM), McCoy's modified medium and mixed media thereof. In the case of using as animal cell culture medium, DMEM/F12 medium is used particularly preferably, although not limited thereto.

Additives such as amino acids, inorganic salts, vitamins, carbon sources or antibiotics can be added to the basal medium for culturing animal cells. There are no particular limitations on the concentrations at which these additives are used, and can be used at concentrations used in ordinary animal cell media.

Examples of amino acids include glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and L-valine.

Examples of inorganic salts include calcium chloride, copper sulfate, iron (II) nitrate, iron sulfate, magnesium chloride, magnesium sulfate, potassium chloride, sodium bicarbonate, sodium chloride, disodium hydrogen phosphate and sodium dihydrogen phosphate.

Examples of vitamins include choline, vitamin A, vitamin B1, vitamin B2, vitamin B3, vitamin B4, vitamin B5, vitamin B6, vitamin B7, vitamin B12, vitamin B13, vitamin B15, vitamin B17, vitamin Bh, vitamin Bt, vitamin Bx, vitamin C (ascorbic acid), vitamin D, vitamin E, vitamin F, vitamin K, vitamin M and vitamin P.

Other examples of additives that may be added include antibiotics such as penicillin, streptomycin, gentamycin or kanamycin, carbon sources such as glucose, galactose, fructose or sucrose, trace metals such as magnesium, iron, zinc, calcium, potassium, sodium, copper, selenium, cobalt, tin, molybdenum, nickel or silicon, stem cell differentiation inducers such as β-glycerophosphoric acid, dexamethasone, rosiglitazone, isobutyl methylxanthine or 5-azacytidine, antioxidants such as 2-mercaptoethanol, catalase, superoxide dismutase or N-acetylcysteine, adenosine-5'-monophosphate, corticosterone, ethanolamine, insulin, reduced glutathione, lipoic acid, melatonin, hypoxanthine, phenol red, progesterone, putrescine, pyruvic acid, thymidine, triiodothyronine, transferrin, lactoferrin, albumin, bovine serum-derived fetuin, sodium bicarbonate, HEPES and other buffers, lipid mix and ITSE (insulin, transferrin, selenium and ethanolamine) mix.

Examples of formulated medium include: medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO—OH Pic, pifithrin-α, SB203580, lithium chloride and Y-27632 to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO-OHPic, pifithrin-aand SB203580 to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, lithium chloride and Y-27632 to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO-OHPic, pifithrin-α, SB203580 and Y-27632 to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO-OHPic, pifithrin-α, SB203580 and lithium chloride to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO-OHPic, SB2035080, lithium chloride and Y-27632 to DMEM/F-12 medium;

medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, pifithrin-α, SB203580, lithium chloride and Y-27632 to DMEM/F-12 medium; and, medium obtained by adding L-glutamine, ascorbic acid, human recombinant albumin, bovine serum-derived fetuin, sodium bicarbonate, HEPES, lipid mix, ITSE mix, transferrin, bFGF, progesterone, hydrocortisone, VO-OHPic, pifithrin-α, lithium chloride and Y-27632 to DMEM/F-12 medium.

There are no particular limitations on the method used to prepare the formulated medium, and the formulated medium can be prepared according to a conventionally known routine method. For example, each of the aforementioned components is added to and mixed into the basal medium for culturing animal cells at room temperature or after warming as necessary.

Although the formulated medium is preferably a liquid, it may also be a solid medium in the form of a gel or agar medium as necessary. According to the formulated medium, mesenchymal stem cells can be seeded and incubated in a culture vessel or culture carrier which the culture surface may or may not be treated.

[Preparation of Culture Supernatant of ROR1-Positive Mesenchymal Stem Cells]

There are no particular limitations on a culture supernatant of the ROR1-positive mesenchymal stem cells of the present invention provided the supernatant is obtained by culturing the aforementioned ROR1-positive mesenchymal stem cells. For example, the aforementioned ROR1-positive mesenchymal stem cells are normally cultured at a suitable cell density and in a suitable medium at a temperature of 30° C. to 37° C. and in an environment containing 2% to 7% $CO_2$ and 5% to 21% $O_2$. Culturing may be carried out using serum-free medium throughout the entire cell incubation period. Here, the explanation of serum-free medium in the previously described section on ROR1-positive mesenchymal stem cells can be applied to the serum-free medium used.

The time at which the culture supernatant is collected is normally 1 to 5 days after, preferably 1 to 4 days after, more preferably 1 to 3 days after, and even more preferably 2 to 3 days after having subcultured the cells for a suitable number of times in consideration of cell status. The culture supernatant may be collected only one time or may be collected on multiple occasions over the course of multiple days.

Furthermore, although a culture supernatant of the ROR1-positive mesenchymal stem cells of the present invention refers to that from which cells and the like have been removed from culture broth (culture broth following culturing) obtained by culturing in a culture broth that allows ROR1-positive mesenchymal stem cells to grow or survive under conditions that allow ROR1-positive mesenchymal stem cells to grow or survive, it also includes that from which at least a portion of components not contributing to the effects of the present invention, such as residual medium components (components of the culture broth prior to culturing remaining in the cultured broth after culturing) or moisture present in the culture broth, have been removed from the culture supernatant, and for the sake of convenience, includes the culture supernatant of the ROR1-positive mesenchymal stem cells in the present description. Furthermore, from the viewpoint of convenience, that from which mesenchymal stem cells have been removed from a culture broth following culturing is preferably used as it is as a culture supernatant.

The culture supernatant of ROR1-positive mesenchymal stem cells in the present invention may also be characterized by, for example, cytokines, nucleic acids such as miRNA or metabolites and the like contained therein.

[Pharmaceutical Composition]

The pharmaceutical composition of the present invention is characterized by containing ROR1-positive mesenchymal stem cells and/or culture supernatant thereof. The ROR1-positive mesenchymal stem cells are cells that have the properties of demonstrating superior inhibitory action on the production of inflammatory cytokines such as IL-6, action that enhances barrier function, migratory capacity and mitochondrial transfer capacity, while also being resistant to oxidative stress and being less susceptible to damage. In addition, the ROR1-positive mesenchymal stem cells are capable of efficiently differentiating into cells having a target function under differentiation conditions while simultaneously maintaining an undifferentiated state. The pharmaceutical composition of the present invention that contains such ROR1-positive mesenchymal stem cells demonstrates excellent preventive or therapeutic effects against various diseases. The pharmaceutical composition of the present invention may also contain other components in addition to ROR1-positive mesenchymal stem cells within a range that does not impair the effects of the present invention.

The pharmaceutical composition of the present invention contains a mesenchymal stem cell population, and all or a portion thereof consists of ROR1-positive mesenchymal stem cells. The ROR1-positive mesenchymal stem cells are as previously described. The ratio of ROR1-positive mesenchymal stem cells in the mesenchymal stem cell population contained in the pharmaceutical composition of the present invention is preferably as high as possible. The aforementioned ratio is preferably 50% or more, more preferably 70% or more, even more preferably 90% or more, particularly preferably 95% or more, and most preferably 99% or more.

[Preparation of Pharmaceutical Composition]

The present invention also includes a method for preparing a pharmaceutical composition used to treat or prevent disease that includes a step for inducing, concentrating or isolating and sorting ROR1-positive mesenchymal stem cells. Examples of the aforementioned disease include diseases selected from the group consisting of cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases and kidney diseases.

The method for preparing a pharmaceutical composition of the present invention includes a step for inducing, concentrating or isolating and sorting ROR1-positive mesenchymal stem cells. There are no particular limitations on the method used in the aforementioned step for inducing ROR1-positive mesenchymal stem cells provided it is a method capable of inducing or enhancing expression of ROR1 in mesenchymal stem cells. For example, a method for inducing expression of ROR1 protein in mesenchymal stem cells using the medium described above is also exemplified as a preferable method. As a result of culturing using the aforementioned formulated medium, 60% or more, preferably 70% or more, more preferably 80% or more, and even more preferably 90% or more of the cells can be induced to ROR1-positive cells, and particularly preferably, the cell population consists of a substantially homogeneous population of ROR1-positive cells.

In addition, examples of methods used in the step for concentrating, isolating and sorting ROR1-positive mesenchymal stem cells include methods using a cell sorter or magnetic beads by using antibody that specifically recognizes ROR1. According to these methods, mesenchymal stem cells expressing ROR1 protein on the cell surface thereof can be selectively concentrated, isolated and sorted.

In addition to the ROR1-positive mesenchymal stem cells and/or culture supernatant thereof acquired according to the aforementioned step for inducing, concentrating or isolating and sorting ROR1-positive mesenchymal stem cells, the pharmaceutical composition of the present invention may also contain ROR1-negative mesenchymal stem cells as well as other cells within a range that does not impair the effects of the present invention, and pharmaceutically acceptable carriers and additives may be contained corresponding the application and form thereof in accordance with routine methods. Examples of such carriers and additives include, but are not limited to, isotonic agents, thickeners, sugars, sugar-alcohols, antiseptics (preservatives), disinfectants or antimicrobial agents, pH adjusters, stabilizers, chelating agents, oily bases, gel bases, surfactants, suspending agents, binders, excipients, lubricants, disintegrating agents, foaming agents, fluidizing agents, dispersants, emulsifiers, buffers, solubilizing agents, antioxidants, sweeteners, sour agents, colorants, flavoring agents, fragrances and fresheners. The following indicates examples of carriers and additives used as typical components.

[Applications of ROR1-Positive Mesenchymal Stem Cells and Pharmaceutical Composition Containing Same of Present Invention]

The pharmaceutical composition of the present invention can be used to prevent and/or treat various diseases, and although there are no particular limitations on the applications thereof, preferable examples include applications based on the actions and functions explained below.

(Action of Enhancing Barrier Function of Culture Supernatant)

A culture supernatant of the ROR1-positive mesenchymal stem cells of the present invention demonstrates an effect that results in superior enhancement of the barrier function of cells in comparison with a culture supernatant of conventional ROR1-negative mesenchymal stem cells. Namely, since a culture supernatant of the ROR1-positive mesenchymal stem cells of the present invention demonstrates a remarkable effect that enables recovery of the barrier function of cells that have been damaged by inflammation, the ROR1-positive mesenchymal stem cells and pharmaceutical composition containing the same of the present invention can be preferably used to treat diseases associated with inflammation. In addition, the ROR1-positive mesenchymal stem cells or culture supernatant thereof can also be used in cosmetic compositions or food compositions and the like.

(Anti-Inflammatory Effect)

The ROR1-positive mesenchymal stem cells of the present invention have an effect that inhibits the production of inflammatory cytokines by macrophages during inflammation. This effect is significantly more potent in comparison with conventional ROR1-negative mesenchymal stem cells. Consequently, the ROR1-positive mesenchymal stem cells and pharmaceutical composition containing the same of the present invention can be preferably used to treat diseases associated with inflammation. In addition, the ROR1-positive mesenchymal stem cells or culture supernatant thereof can also be used in cosmetic compositions or food compositions and the like.

(Antitumor Effect)

The ROR1-positive mesenchymal stem cells of the present invention have superior migratory capacity in comparison with ROR1-negative mesenchymal stem cells. In addition, a culture supernatant of the ROR1-positive mesenchymal stem cells of the present invention demonstrates a high level of activity that inhibits the migration of cancer cells in comparison with a culture supernatant of ROR1-negative mesenchymal stem cells. Namely, the ROR1-positive mesenchymal stem cells of the present invention are thought to be able to suitably migrate to a site of action due to the superior migratory capacity thereof, and are thought be able to inhibit infiltration and metastasis of cancer cells by further inhibiting migration of cancer cells and the like at a site of action. Thus, a pharmaceutical composition containing the ROR1-positive mesenchymal stem cells of the present invention and a pharmaceutical composition containing a culture supernatant of the ROR1-positive mesenchymal stem cells of the present invention is preferably used as a pharmaceutical that demonstrates antitumor effects.

(Action as Mitochondrial Transfer Agent)

The ROR1-positive mesenchymal stem cells of the present invention have superior mitochondrial transfer capacity, therefore, demonstrate superior effects on symptoms accompanying each disease, aging and stress by transferring mitochondria to cells that have mitochondrial dysfunction and undergone a decrease in mitochondrial activity. Thus, the ROR1-positive mesenchymal stem cells of the present invention or a pharmaceutical composition containing culture supernatant thereof is preferably used as a mitochondrial transfer agent for improving, treating and/or preventing symptoms accompanying each disease, aging and stress by transferring mitochondria to cells that have mitochondrial dysfunction and undergone a decrease in mitochondrial activity. Examples of such diseases and symptoms include, but are not limited to, diseases and symptoms relating to cardiac myocytes, alveolar epithelial cells, renal tubule cells, astrocytes, bronchial smooth muscle cells, vascular smooth muscle cells, vascular endothelial cells, immune cells (such as macrophages), epidermal stem cells, dermal fibroblasts and corneoconjunctival epithelial stem cells, and particularly preferably include diseases and symptoms relating to cardiac myocytes, dermal fibroblasts and bronchial smooth muscle cells.

Examples of diseases for which the ROR1-positive mesenchymal stem cells of the present invention and a pharmaceutical composition containing the same can be used as a pharmaceutical include cartilage degradation, rheumatoid arthritis, psoriatic arthritis, spondylarthritis, osteoarthrosis, gout, psoriasis, multiple sclerosis, amyotrophic lateral sclerosis, Alzheimer's disease, Parkinson's disease, congestive heart failure, cerebral infarction, stroke, aortic valve stenosis, kidney failure, lupus, pancreatitis, allergies, fibrosis, anemia, atherosclerosis, restenosis, complications associated with chemotherapy and/or radiotherapy, type I diabetes, type II diabetes, autoimmune hepatitis, hepatitis C, primary biliary cirrhosis, primary sclerosing cholangitis, fulminant hepatitis, celiac disease, non-specific colitis, allergic conjunctivitis, diabetic retinopathy, Sjogren's syndrome, uveitis allergic rhinitis, asthma, asbestosis, silicosis, chronic obstructive pulmonary disease, chronic granulomatous inflammation, alveolar fibrosis, sarcoidosis, glomerular nephritis, vasculitis, dermatitis, HIV-related cachexia, cerebral malaria, ankylosing spondylitis, leprosy, pulmonary fibrosis, fibromyalgia, esophageal cancer, gastroesophageal reflux, Barrett's esophagus, gastric cancer, duodenal cancer, small intestine cancer, appendix cancer, large bowel cancer, colon cancer, rectal cancer, anal cancer, pancreatic cancer, liver cancer, gallbladder cancer, spleen cancer, renal cancer, bladder cancer, prostate cancer, testicular cancer, uterine cancer, ovarian cancer, breast cancer, lung cancer and thyroid cancer.

Although there are no particular limitations thereon, examples of administration methods in the case of using the pharmaceutical composition of the present invention as a pharmaceutical preferably include intravascular administration (and preferably intravenous administration), intraperitoneal administration, intestinal administration and subcutaneous administration, with intravascular administration being more preferable.

Although the dosage (dose) of the pharmaceutical composition of the present invention can be varied according to the status of the patient (such as body weight, age, symptoms or general condition) and the drug form of the pharmaceutical composition of the present invention, from the viewpoint of demonstrating adequate preventive or therapeutic effects, a high dosage is preferable, while on the other hand, from the viewpoint of inhibiting adverse reactions, a low dosage tends to be preferable. Normally, in the case of administration to an adult, the dosage in terms of the number of cells is $5\times10^2$ to $1\times10^{12}$ cells/administration, preferably $1\times10^4$ to $1\times10^{11}$ cells/administration, and more preferably $1\times10^5$ to $1\times10^{10}$ cells/administration. Furthermore, this dosage may be administered in a single dose, may be administered in multiple doses, or may be divided into a plurality of administrations. In addition, normally in the case of administration to an adult, the dosage in terms of the number of cells per body weight is $1\times10$ to $5\times10^{10}$ cells/kg, preferably $1\times10^2$ to $5\times10^9$ cells/kg, and more preferably $1\times10^3$ to $5\times10^8$ cells/kg. Furthermore, this dosage may be administered in a single dose, may be administered in multiple doses, or may be divided into a plurality of administrations.

The present invention includes a method for preventing or treating a disease that is characterized by the use of ROR1-positive mesenchymal stem cells or a pharmaceutical composition containing ROR1-positive mesenchymal stem cells. Examples of the aforementioned disease include cancer, precancerous symptoms, inflammatory diseases, immune diseases, neurodegenerative diseases, metabolic diseases, cardiovascular diseases, cerebrovascular diseases, bone diseases, gastrointestinal diseases, lung diseases, liver diseases and kidney diseases.

Examples

Although the following provides a detailed explanation of the present invention through examples thereof, the present invention is not limited to the following examples.

<Preparation of ROR1-Positive Mesenchymal Stem Cells>

Umbilical cord-derived mesenchymal stem cells (UC-MSC: Umbilical Cord-derived Mesenchymal Stem Cells Wharton's Jelly (HMSC-WJ), FC-0020, Lifeline Corp.) were conditioned with the recommended medium of Lifeline Corp. under conditions of 37° C. and 5% $CO_2$ followed by carrying out subculturing in the same medium in accordance with routine methods and using the resulting UC-MSC in the experiments indicated below.

After seeding the aforementioned UC-MSC at 6700 cells/$cm^2$ and culturing for 4 days, the cells were washed twice with D-PBS(-) and then recovered using 0.025% trypsin. After centrifuging for 5 minutes at 200 G and 4° C., the cells were re-suspended in 1% BSA/D-PBS solution. PE anti-human ROR1 (BD Biosciences Inc., #564474) or mouse IgG2b PE, κ Isotype control (Biolegend Inc., #401208) were each added at a concentration of 5 μl/100 μl and allowed to react for 1 hour. After washing the cells three times with 1% BSA/D-PBS solution, the cells were re-suspended in 1% BSA/D-PBS followed by carrying out cell sorting with the Sony SH800Z. Each group of cells was seeded in a 6-well plate or 96-well plate at $1\times10^4$ cells/$cm^2$ to $3\times10^4$ cells/$cm^2$ using the aforementioned recommended medium.

The following tests were carried out using the resulting ROR1-positive MSC (R posi), ROR1-negative MSC (R nega) and, as necessary, ROR1-positive MSC and ROR1-negative MSC mixed at a ratio of 1:1 (R mix), and MSC on which sorting was not carried out (R unsorted). Furthermore, in this testing, the cell population recovered as ROR1-positive MSC had the possibility of also containing ROR1-negative MSC.

(Cell Migration Test)

The ROR1-positive MSC and ROR1-negative MSC obtained according to the aforementioned sorting were additionally cultured for 2 days in the recommended medium of Lifeline Corp. followed by recovering the cells by treating with trypsin in accordance with routine methods. The recovered cells were suspended in DMEM/F12 (containing 0.2% FBS (MP Biomedicals LLC) and 1% antibiotic-antimycotic (Gibco Corp., 15240-062) and seeding aliquots containing about $3.0 \times 10^4$ cells in 200 μL of medium in the upper compartment wells of a 24-well Boyden chamber (Corning Inc., 3422). 550 μL of DMEM/F12 (containing 10% FBS and 1% antibiotic-antimycotic) were added to the lower compartment wells followed by culturing for 5 hours at 37° C. in an environment containing 5% carbon dioxide gas and 95% air. Following culturing, the medium was removed from the wells of the upper compartments and lower compartments followed by washing with PBS(−), adding 500 μL of methanol (Wako Pure Chemical Industries, Ltd., 134-01833) cooled to −30° C. to the lower compartment wells and allowing to stand undisturbed for 10 minutes at −30° C. After removing the methanol and washing with PBS(−), 500 μL of 1% crystal violet solution (obtained by preparing a two-fold dilution of Gram stain reagent solution 1 (Muto Pure Chemicals Co., Ltd., 41131) with 20% ethanol/water) were added to the lower compartment followed by staining for 10 minutes at room temperature. After removing the upper compartment wells and washing with running water, the cells remaining on the top of the membrane were completely removed using a cotton swab. The membrane was then cut up using a scalpel and placed in the wells of a 96-well plate followed by lysing the cells by adding 50 μL of 1% aqueous SDS solution. The membrane was then removed and absorbance (590 nm, control wavelength: 650 nm) was measured with a plate reader (Molecular Probe Inc.). The measured values represent values proportional to the number of cells that migrated from the upper compartment wells to the lower compartment wells. The results are shown in FIG. 1.

As shown in FIG. 1, ROR1-positive MSC (R posi) were determined to demonstrate remarkably high migratory capacity in comparison with ROR1-negative MSC (R nega).

(Oxidative Stress Resistance Test)

Each of the ROR1-positive MSC (R posi), ROR1-negative MSC (R nega), ROR1-positive MSC and ROR1-negative MSC mixed at a ratio of 1:1 (R mix) and MSC not subjected to sorting (R unsorted) obtained according to the aforementioned method were re-seeded after aligning cell density followed by treating for 1 hour in $H_2O_2$/HBSS solution having the concentrations shown in FIG. 3 two days later and comparing the numbers of cells 24 hours after returning to the original medium by nuclear staining with Hoechst 33342 and analysis of fluorescence images thereof.

Figure 2:
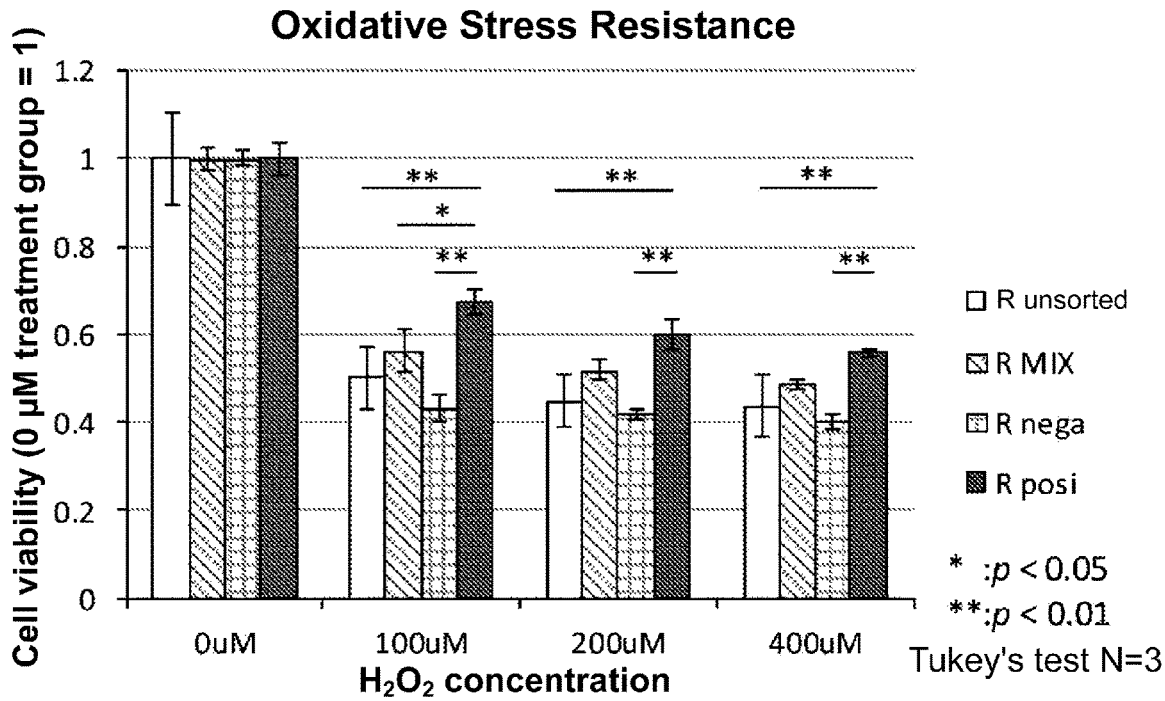
FIG. 2 is a bar graph indicating the resistance to oxidative stress of ROR1-positive mesenchymal stem cells.

As shown in FIG. 2, although the UC-MSC demonstrated a reduction in the number of cells as a result of being impaired by the $H_2O_2$/HBSS treatment, resistance to impairment by treatment with $H_2O_2$/HBSS solution of the ROR1-positive MSC (R posi) was significantly higher in comparison with the ROR1-negative MSC (R nega) and the MSC that were not subjected to sorting (R unsorted), thereby suggesting that the ROR1-positive MSC were less susceptible to oxidative stress and inhibited reductions in the number of cells.

(Mitochondrial Transfer Test)

Figure 4:
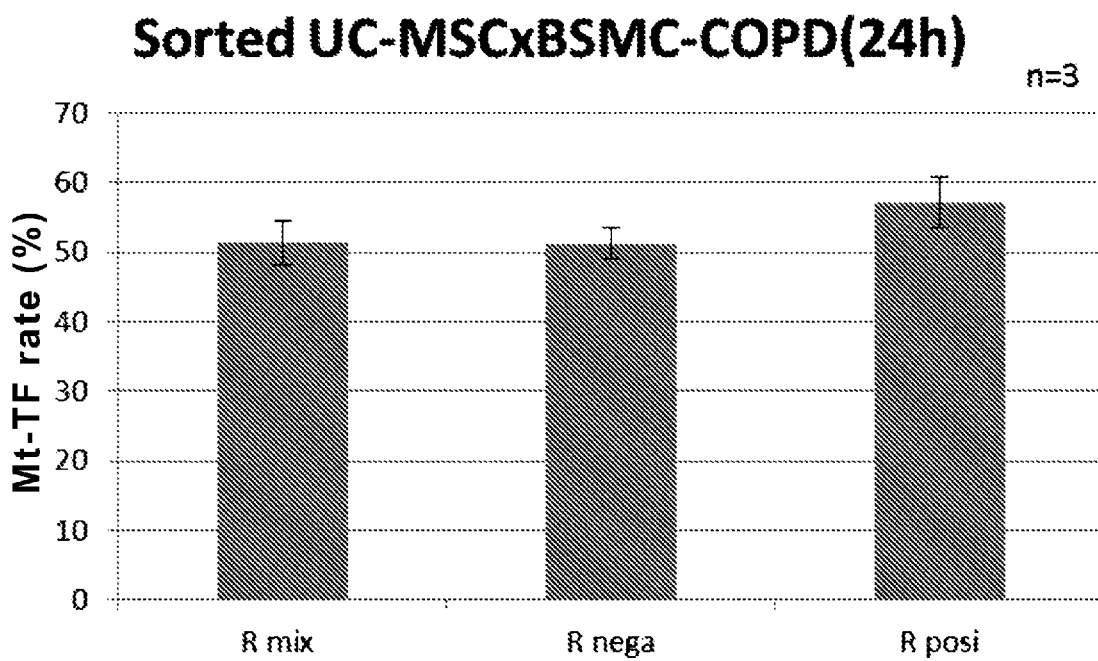
FIG. 4 is a bar graph indicating the mitochondrial transfer capacity of ROR1-positive mesenchymal stem cells in human bronchial smooth muscle cells of chronic obstructive pulmonary disease.
Figure 5:
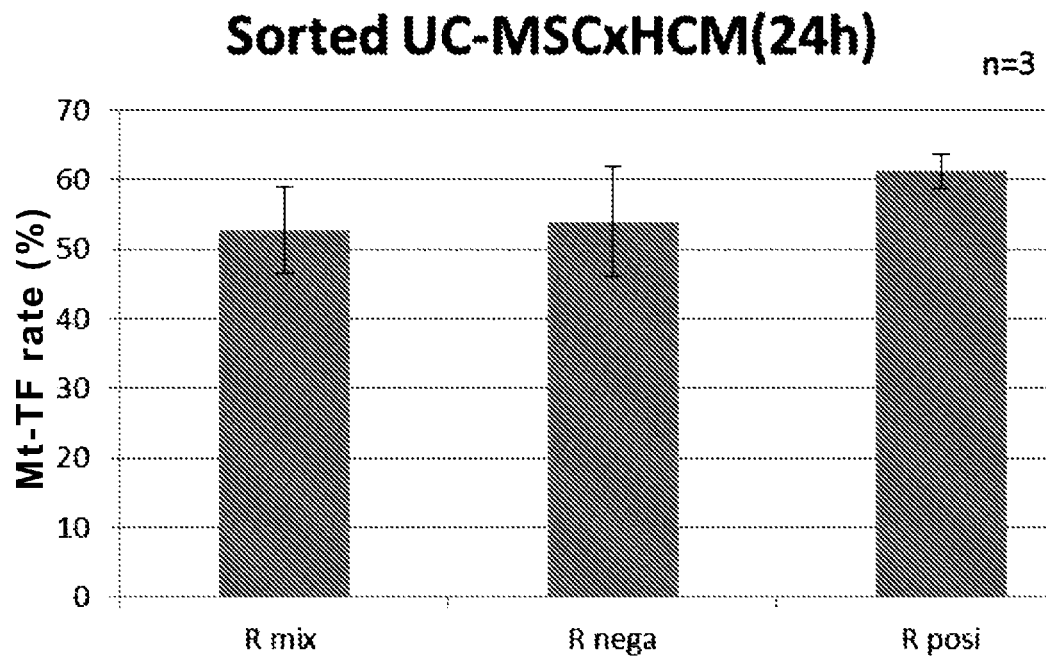
FIG. 5 is a bar graph indicating the mitochondrial transfer capacity of ROR1-positive mesenchymal stem cells in human cardiac myocytes.

Each of the ROR1-positive MSC (R posi), ROR1-negative MSC (R nega), ROR1-positive MSC and ROR1-negative MSC mixed at a ratio of 1:1 (R mix) and MSC not subjected to sorting (R unsorted) obtained according to the aforementioned method were seeded in a 6-well plate (Corning Inc., Cell Bind 3335) at $1 \times 10^5$ cells/well. Two days later, the cells were detached by treating with trypsin/EDTA (Kurabo Industries Ltd., HK-3120) and the re-seeded. Mitochondrial staining reagent (Molecular Probes MitoTracker® Green FM (M7514, Life Technologies Corp.) diluted 1/1,000 with HBSS(+)) was added to a flask of US-MSC cells serving as the mitochondria supply source and incubated for 30 minutes at 37° C., followed by the addition of a cytoplasm staining reagent (Invitrogen CellTrace™ Far Red Cell Proliferation Kit (Life Technologies Corp., C34564) diluted to 1/7,000 with HBSS(+)) to a flask of cells serving as mitochondria recipients and incubating for 1 hour at 37° C. After staining, the medium was replaced and after incubating overnight at 37° C., the cells were washed three times with HBSS(+) on the following day followed by detaching the cells with trypsin/EDTA. The detached cells were washed with HBSS(+) and both cells were seeded into a plate (96-well plate) at 2,000 cells/well each followed by initiation of co-culturing. On the following day, a nuclear staining reagent was diluted 1/1000 with PBS(−) and used to replace the media in the wells. After allowing to stand at room temperature for 15 minutes, images of the wells were photographed with Image Xpress (at 16 fields/well). The cells were then analyzed with a cell counting program* to calculate the mitochondrial transfer rate. The results are shown in FIGS. 3 to 5.

The following cells were used as recipient cells.

ROR1-positive MSC and ROR1-negative MSC prepared in the manner described above.

BSMC-COPD cells (human bronchial smooth muscle cells of chronic obstructive pulmonary disease (Lonza Group Ltd., 00195274); a combination of SmGM™-2 medium, Bullet Kit (Lonza Group Ltd., CC-3182) and 1% antibiotic-antimycotic (Gibco Corp.) was used to culture the BSMC-COPD cells.

Human cardiac myocytes (HCM, PromoCell GmbH); Myocyte Basal Medium (PromoCell GmbH, C-22170) and Myocyte Growth Medium Supplement Pack (PromoCell GmbH, C-39270) were used to culture the HCM.

Analyses using the cell counting program* were carried out in the manner indicated below.

(1) Nuclei are identified and counted (counted number of nuclei=counted number of cells) by observing with a filter that recognizes nuclear staining such as DAPI filter.

(2) The cytoplasm of cells (recipients) that have received transfer of mitochondria are identified and counted (by, for example, defining cells that are stained red as recipient cells) by observing with a filter that recognizes recipient cell staining such as a Cy5 filter.

(3) Cells having mitochondria (donor cells) are identified and counted (by, for example, defining cells that are stained green as donor cells) by observing with a filter that recognizes mitochondrial staining.

(4) Mitochondrial transfer rate (%) can then be calculated according to the equation indicated below. In addition, the cytotoxicity of a drug can be evaluated by counting the number of cells of (1).

Calculation formula: (Number of cells of(2) and(3)/number of cells of(2)× 100

Figure 3:
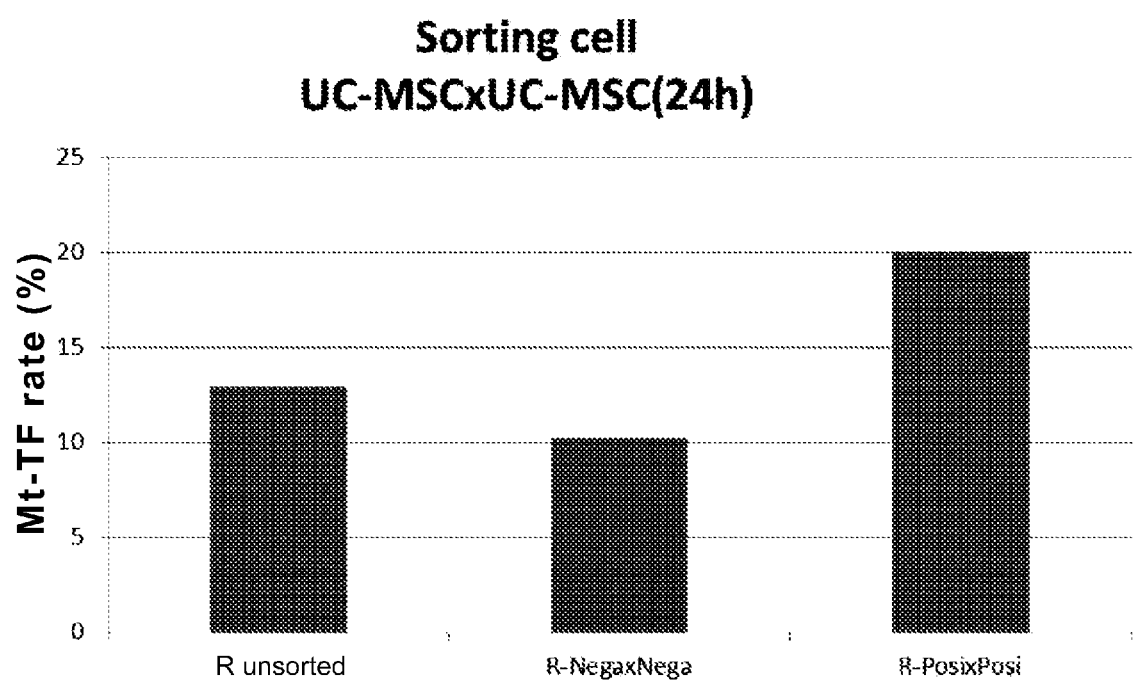
FIG. 3 is a bar graph indicating the mitochondrial transfer capacity of ROR1-positive mesenchymal stem cells.

As shown in FIG. 3, ROR1-positive MSC (R posi) exhibited remarkably high mitochondrial transfer capacity in comparison with the ROR1-negative MSC (R nega) and the MSC not subjected to sorting (R unsorted). In addition, as shown in FIG. 4, the mitochondrial transfer rate to BSMC-COPD cells (human bronchial smooth muscle cells of chronic obstructive pulmonary disease) was remarkably higher for ROR1-positive MSC than ROR1-negative MSC. Moreover, as shown in FIG. 5, mitochondrial transfer rate to HCM (human cardiac myocytes) was determined to be remarkably high for ROR1-positive MSC in comparison with ROR1-negative MSC.

On the basis of the above results, ROR1-positive MSC were determined to demonstrate superior migration capacity as well as potent resistance to oxidative stress in comparison with ROR1-negative MSC. In addition, since ROR1-positive MSC demonstrate high rates of transferring their own mitochondria to a strain of human bronchial smooth muscle cells of chronic obstructive pulmonary disease in the form of BSMC-COPD cells and a strain of human cardiac myocytes in the form of HCM cells, ROR1-positive MSC are thought to be effective for treating or preventing chronic obstructive pulmonary disease and heart disease. In addition, ROR1-positive MSC are also considered to be able to be widely used against symptoms accompanying diseases and aging associated with impaired mitochondrial function or decreased mitochondrial activity in addition to the aforementioned diseases.

(Anti-Inflammatory Effect)

ROR1-positive MSC and ROR1-negative MSC obtained according to the aforementioned method were cultured for 48 hours in 0.2% FBS-DMEM/F12 medium followed by recovery of the culture supernatant for use in the following testing.

A medium was prepared by diluting a 0.5 mM DMSO solution of Calcein-AM staining reagent 1,000-fold with 10% FCS DMEM. The Calcein-AM-containing medium was added to mouse macrophage cell line Raw264.7, and after pre-culturing for 3 hours at 37° C. in 5% $CO_2$, the cells were seeded in 48-well plates at $5 \times 10^5$ cells/well.

On the following day, one-half the amount of culture supernatant was added followed 4 hours later by the addition of LPS to a concentration of 100 ng/mL. The culture supernatant was recovered 17 to 18 hours later. The amount of IL-6 in the culture supernatant was measured by ELISA (mIL-6 ELISA, R&D Duoset ELISA Kit, R&D Systems Inc., DY406-05). Furthermore, after recovering the culture supernatant, the number of cells corresponding to the amount of IL-6 was corrected by measuring the fluorescence value of Calcein-AM preliminarily taken up by the Raw264.7 cells and subtracting that value. The results are shown in FIG. 6.

Figure 6:
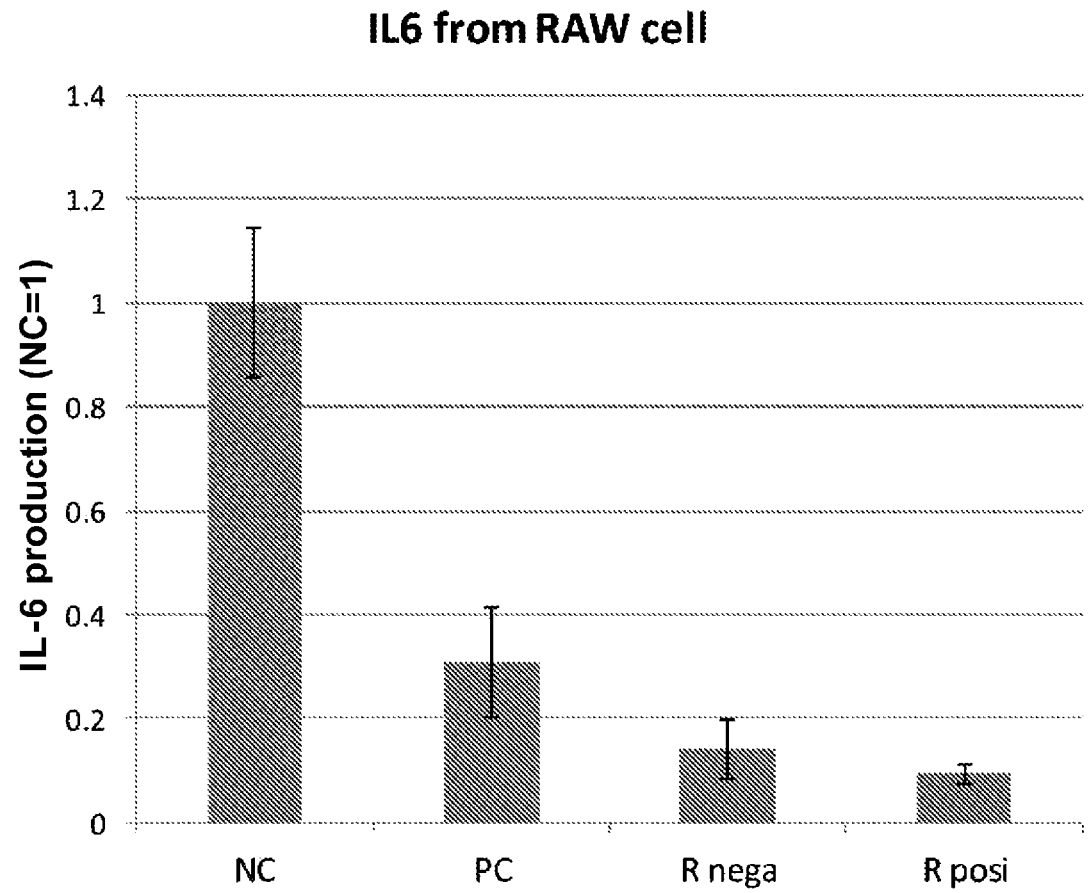
FIG. 6 is a bar graph indicating the anti-inflammatory effects of culture supernatants of ROR1-positive mesenchymal stem cells.

As shown in FIG. 6, when the culture supernatant of ROR1-positive MSC was added, production of the inflammatory cytokine produced by mouse macrophage cell line Raw264.7 in the form of IL-6 was more inhibited in comparison with the case of having added culture supernatant of ROR1-negative MSC.

<Induction of ROR1-Expressing Cells>

(Preparation of Formulated Medium)

The basic medium was prepared as shown in Table 1 below. More specifically, the components described in the following Table 1 were added to DMEM/F12 medium at the concentrations described in the table.

TABLE 1

| Component | Concentration |
| --- | --- |
| DMEM/F-12 | — |
| L-Glutamine | 4 mM |
| Ascorbic acid | 50 µg/ml |
| Human recombinant Albumin | 4 mg/ml |
| Bovine Fetuin | 1 mg/ml |
| NaHCO₃ | 20.5 mM |

TABLE 1-continued

| Component | Concentration |
| --- | --- |
| HEPES | 4.9 mM |
| Lipids (Chemically Defined Lipid Concentrate) | 0.1% (v/v) |
| ITSE | Insulin: 10 µg/ml, Transferrin: 5.5 µg/ml, Sodium selenite: 6.7 ng/ml, Ethanolamine: 2 µg/ml |
| bFGF | 2 ng/ml |
| Progesterone | 0.018 µM |
| Hydrocortisone (50 µM) | 100 nM |

LiCl (Wnt signaling activator) at 250 µM, Y-27632 (ROCK inhibitor) at 100 nM, pifithrin-α(p53 inhibitor) at 10 µM, VO-OHPic (PTEN inhibitor) at 500 nM and SB203580 (p38 inhibitor) at 100 nM were each added to the basic medium prepared above to prepare a formulated medium. This medium was then used to culture umbilical cord-derived mesenchymal stem cells and adipose-derived mesenchymal stem cells to induce ROR1-positive mesenchymal stem cells. Furthermore, a conventionally known mesenchymal stem cell medium in the form of the recommended medium of Lifeline Corp. was used as a control.

<Culturing and Evaluation of Umbilical Cord-Derived Mesenchymal Stem Cells and Adipose-Derived Mesenchymal Stem Cells>

(Test 1)

Figure 7:
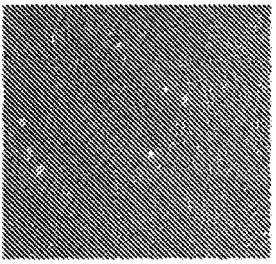
FIG. 7 depicts photomicrographs of umbilical cord-derived mesenchymal stem cells on day 7 of culturing and adipose-derived mesenchymal stem cells on day 8 of culturing in recommended medium or formulated medium.
Figure 8:
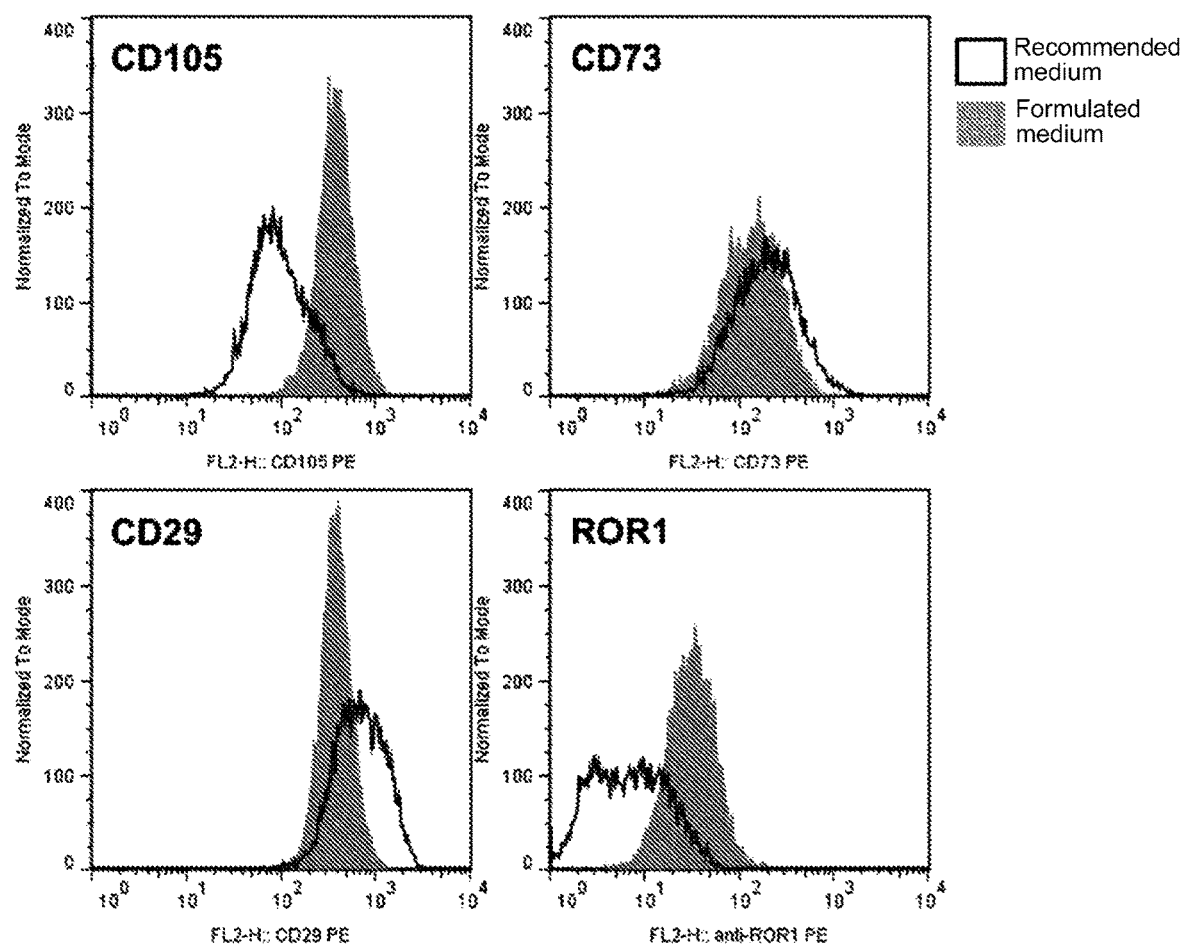
FIG. 8 depicts graphs indicating cell surface markers of umbilical cord-derived mesenchymal stem cells on day 8 of culturing in recommended medium or formulated medium.
Figure 9:
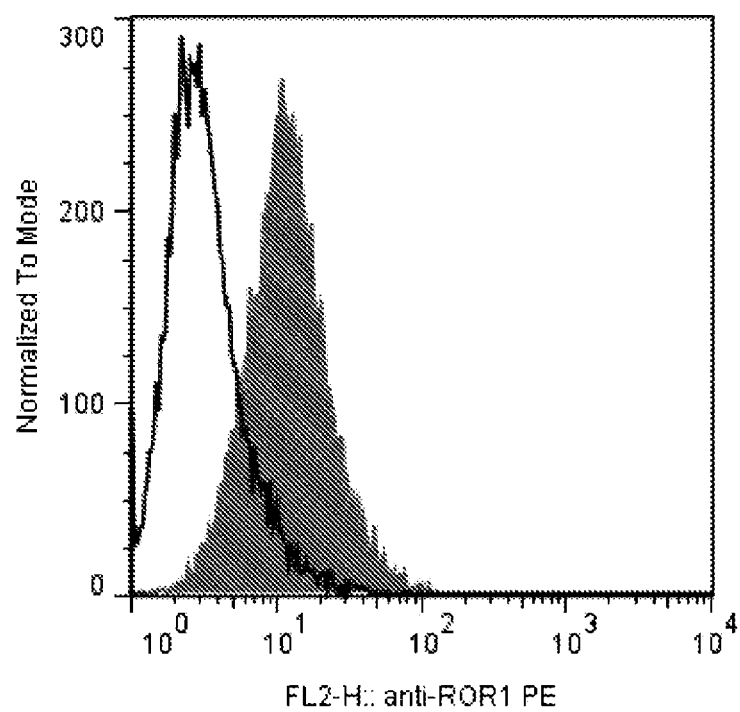
FIG. 9 is a graph indicating expression of ROR1 by adipose-derived mesenchymal stem cells on day 8 of culturing in recommended medium or formulated medium.
Figure 10:
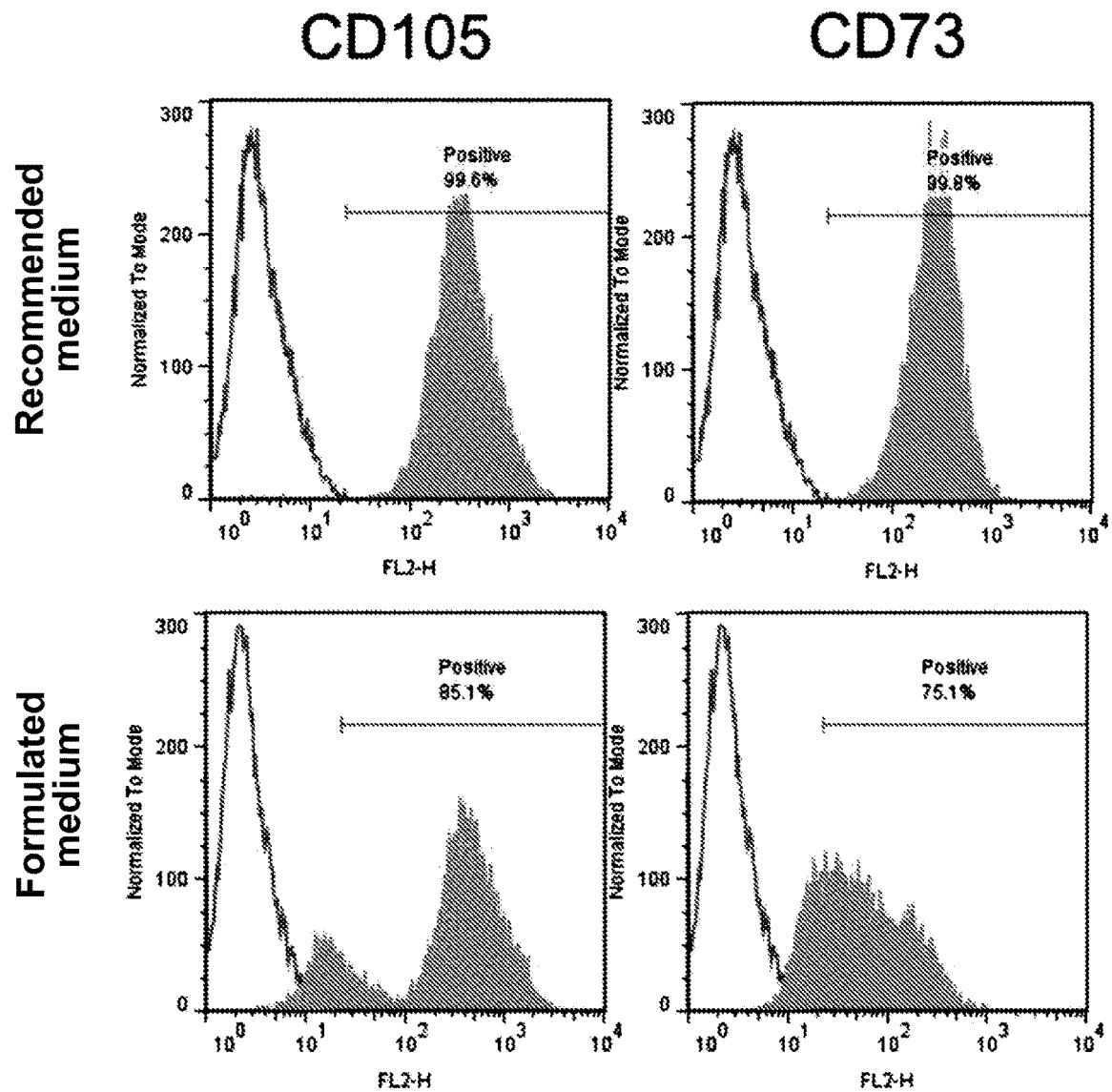
FIG. 10 depicts graphs indicating expression of cell surface markers by adipose-derived mesenchymal stem cells on day 8 of culturing in recommended medium or formulated medium.

Umbilical cord-derived mesenchymal stem cells (UC-MSC: Umbilical Cord-derived Mesenchymal Stem Cells Wharton's Jelly (HMSC-WJ), FC-0020, Lifeline Corp.; Primary Umbilical Cord-Derived Mesenchymal Stem Cells: Normal Human, PCS-500-010, ATCC; Human Umbilical Mesenchymal Stem Cells (HUMSC), 7530, Sciencell Research Laboratories, Inc.) and adipose-derived mesenchymal stem cells (AD-MSC: Adipose-Derived Mesenchymal Stem Cells, FC-0034, Lifeline Corp.) were conditioned with the recommended medium of corresponding company under conditions of 37° C. and 5% $CO_2$ followed by seeding in CellBIND flasks at a density of 5,000 cells/cm². The medium was replaced with the recommended medium, or the formulated medium on the following day ($1 \times 10^5$ cells/well, 6-well plates). Each of the cells was re-seeded in the same manner three days later and the morphology of the cells after culturing for a total of 7 days (UC-MSC) or 8 days (AD-MSC) is shown in FIG. 7. After similarly culturing for an additional 2 days (total of 8 days), the cells were analyzed for various surface cell markers including ROR1 by FACS (FIG. 8: UC-MSC, FIG. 9: AD-MSC, FIG. 9 shows only expression of ROR1). In the drawings, white areas indicate expression of each cell surface marker by cells cultured in the recommended medium, while gray areas indicate expression of each cell surface marker by cells cultured in the formulated medium. In addition, expression of cell surface markers by the UC-MSC and AD-MSC cells after culturing for 8 days was analyzed by FACS, and those results are shown in FIG. 10 (AD-MSC) and FIG. 11 (UC-MSC).

In contrast to AD-MSC being somewhat smaller and rounded and exhibiting favorable status in the case of using the formulated medium in comparison with the recommended medium, the cells appeared to be long and narrow and were judged to exhibit a somewhat poor status in the case of using the recommended medium. However, in contrast to AD-MSC cultured in the recommended medium exhibiting a single high peak for expression of surface markers CD105 and CD73, culturing in the medium of Example 1 resulted in a decrease in the expression of CD105 in some cells and the appearance of two expression peaks. In addition, the expression level of CD73 decreased overall (FIG. 10). The recommended medium was therefore considered to be suitable for maintaining AD-MSC in an undifferentiated state.

Figure 11:
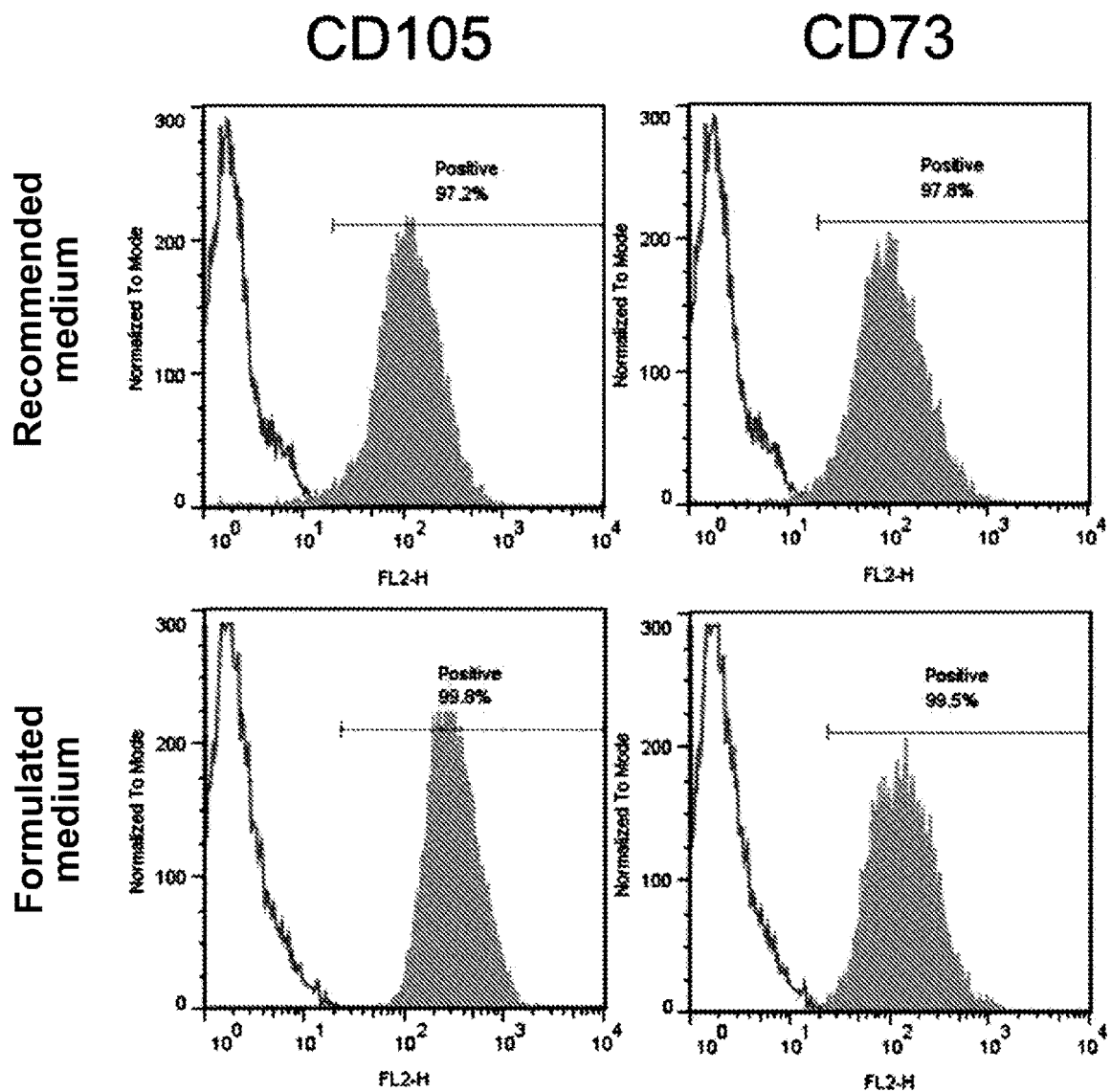
FIG. 11 depicts graphs indicating expression of cell surface markers by umbilical cord-derived mesenchymal stem cells on day 8 of culturing in recommended medium or formulated medium.

On the other hand, the morphology of the UC-MSC was such that the cells appeared smaller and more rounded and exhibited favorable status in the case of the formulated medium as shown in FIG. 7. In addition, as shown in FIGS. 8 and 9, the UC-MSC and AD-MSC cultured for 8 days in the formulated medium demonstrated a remarkable increase in the ratio of ROR1-positive MSC in comparison with each of the cells cultured in the recommended medium, and the expression level of ROR1 was higher. In addition, as shown in FIGS. 8, 10 and 11, culturing the cells in the formulated medium resulted in higher expression peaks for CD105 and CD73, and the cells were judged to able to be more effectively maintained in an undifferentiated state.

(Test 2)

After conditioning umbilical cord-derived mesenchymal stem cells (UC-MSC: Umbilical Cord-derived Mesenchymal Stem Cells Wharton's Jelly (HMSC-WJ), FC-0020, Lifeline Corp.) with the recommended medium of Lifeline Corp. under conditions of 37° C. and 5% $CO_2$, the medium was replaced with the recommended medium of Lifeline Corp. or the formulated medium ($1\times10^5$ cells/well, 6-well plates). The cells were subcultured every 2 to 3 days and then analyzed for expression of cell surface markers (CD29, CD73, CD90, CD105 and CD166) by FACS on day 11 from the time of medium replacement. The results are shown in FIGS. 12 and 13.

Figure 12:
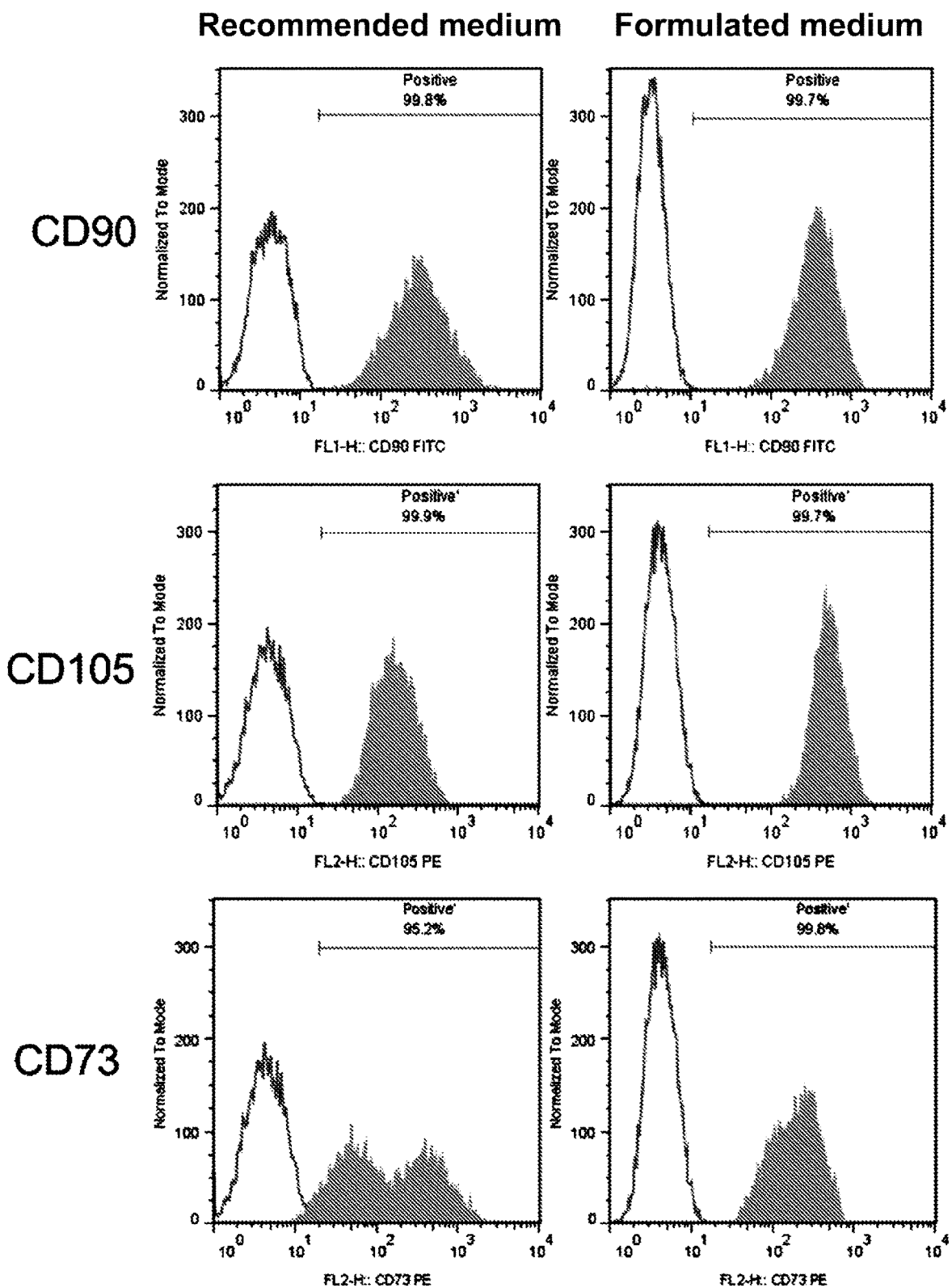
FIG. 12 depicts graphs indicating expression of cell surface markers by umbilical cord-derived mesenchymal stem cells on day 11 of culturing in recommended medium or formulated medium.
Figure 13:
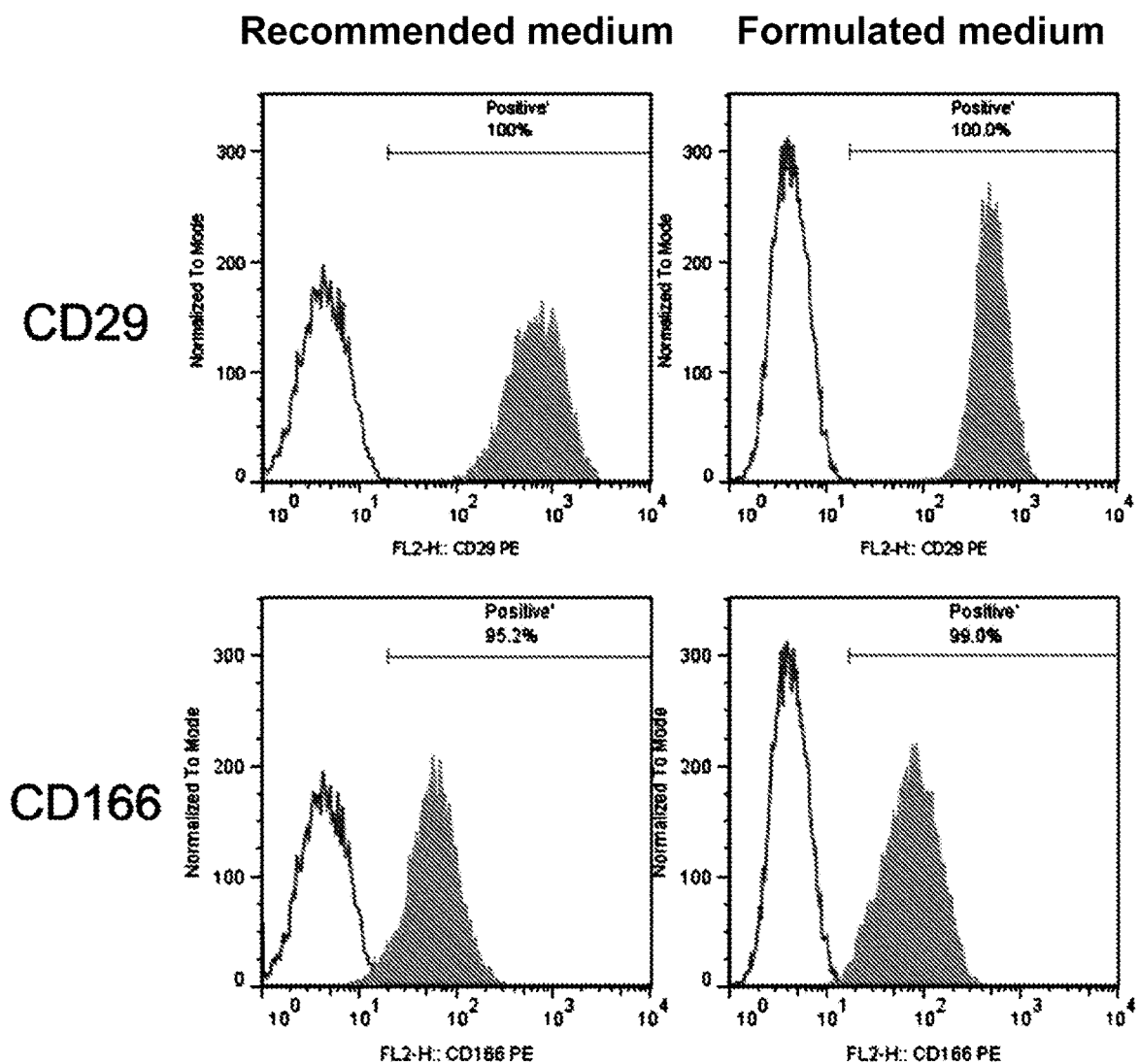
FIG. 13 depicts graphs indicating expression of cell surface markers by umbilical cord-derived mesenchymal stem cells on day 11 of culturing in recommended medium or formulated medium.

As shown in FIGS. 12 and 13, expression of surface markers CD73 and CD166 was higher for UC-MSC cultured in the formulated medium in comparison with having been cultured in the recommended medium, and the peak for CD29 was more uniform. Culturing in the formulated medium was judged to be able to more effectively maintain US-MSC in an undifferentiated state.

(Test 3) Intracellular Expression of mRNA

Umbilical cord-derived mesenchymal stem cells (UC-MSC: Umbilical Cord-derived Mesenchymal Stem Cells Wharton's Jelly (HMSC-WJ), FC-0020, Lifeline Corp.; Umbilical Cord-Derived Mesenchymal Stem Cells, Sciencell Research Laboratories, Inc.; or Umbilical Cord-Derived Mesenchymal Stem Cells, ATCC) were conditioned with the recommended medium of each manufacturer under conditions of 37° C. and 5% $CO_2$ followed by replacing the medium with the recommended medium of each manufacturer or the formulated medium ($1\times10^5$ cells/well, 6-well plates). After subculturing every 2 to 3 days, the cultured cells were recovered followed by isolation of mRNA in accordance with routine methods. More specifically, total RNA was isolated using the RNeasy Mini Kit (Qiagen Inc., 74109) followed by carrying out reverse transcription using the ReverTra Ace qPCR Kit Master Mix with gDNA Remover (Toyobo Co., Ltd., FSQ-301) to synthesize cDNA. Gene expression analysis was carried out by real-time PCR using the synthesized cDNA as a template with TaKaRa Ex Taq (Takara Corp., RR039A) by using primers for each of the genes of ROR1, MT1X, NID2, ANKRD1, CPA4 and DKK1. In addition, expression levels were corrected by using GAPDH and 18 s as internal control genes. The results are shown in FIG. 14.

Figure 14:
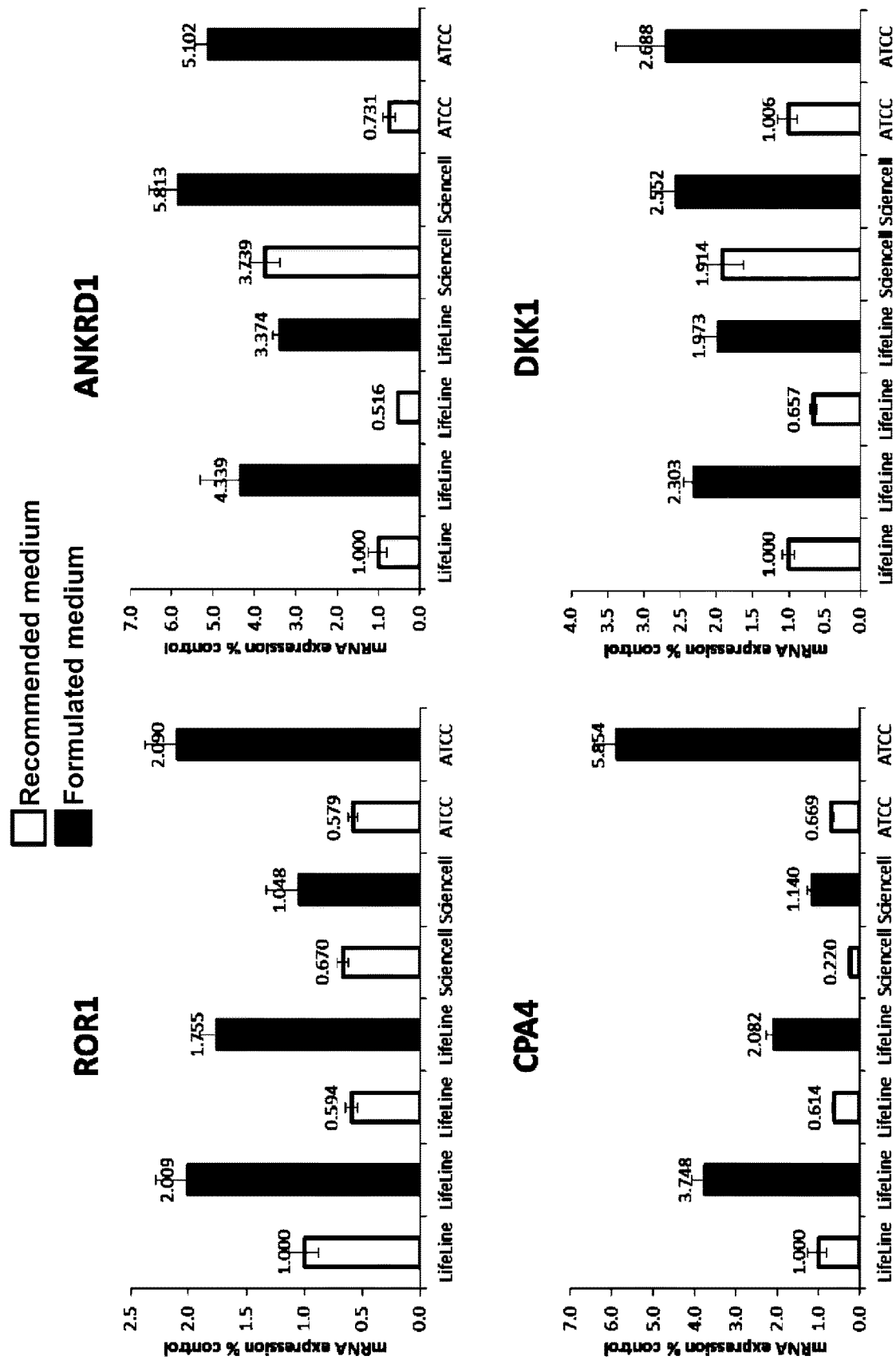
FIG. 14 depicts bar graphs indicating a comparison of gene expression between umbilical cord-derived mesenchymal stem cells cultured in formulated medium and umbilical cord-derived mesenchymal stem cells cultured in recommended medium.

Cells obtained by culturing UC-MSC in the formulated medium demonstrated increased expression of genes ROR1, ANKRD1, CPA4 and DKK1 in comparison with each of the aforementioned cells cultured in the recommended medium (FIG. 14). Furthermore, increases in the expression of genes MT1X and NID2 were observed for UC-MSC from Lifeline Corp. and ATCC cultured in the formulated medium in comparison with the case of having cultured each of the aforementioned cells in the recommended medium in the same manner as the aforementioned four genes.

(Test 4) Intracellular Expression Level of miRNA

After conditioning umbilical cord-derived mesenchymal stem cells (UC-MSC: Umbilical Cord-derived Mesenchymal Stem Cells Wharton's Jelly (HMSC-WJ), FC-0020, Lifeline Corp.) with the recommended medium of Lifeline Corp. under conditions of 37° C. and 5% $CO_2$, the medium was replaced with the recommended medium of Lifeline Corp. or the formulated medium ($1\times10^5$ cells/well, 6-well plates). The cells were subcultured every 2 to 3 days and then recovered on day 8 from the time of medium replacement. mRNA was prepared from the recovered cells according to the same method as that used in the aforementioned Test 7 followed by analyzing expression of miRNA in the cells with an miRNA array (miScript miRNA PCR array: MIHS-105Z and miHS-117Z (Inflammatory Response, Autoimmunity and Fibrosis, Qiagen Inc.). The results were analyzed by dividing the expression level of each type of miRNA in cells obtained by culturing in the formulated medium by the expression level of each miRNA in cells obtained by culturing in the recommended medium (fold change value). The same test was carried out twice.

As a result of analyzing a total of about 150 types of miRNA, UC-MSC cultured in the formulated medium were determined to express has-let-7e-5p, hsa-miR-132-3p, hsa-miR-196a-5p, hsa-miR-324-3p, hsa-miR-328-3p, hsa-miR-382-5p, hsa-let-7d-5p, hsa-miR-145-5p, hsa-miR-181a-5p, hsa-miR-29b-3p, hsa-miR-34a-5p, hsa-miR-199b-5p and hsa-miR-503-5p. In addition, examples of miRNA for which expression by UC-MSC cultured in the formulated medium tended to be particularly increased in comparison with UC-MSC cultured in the recommended medium included hsa-let-7e-5p, hsa-miR-132-3p, hsa-miR-196a-5p, hsa-miR-324-3p, hsa-miR-328-3p, hsa-miR-382-5p and hsa-let-7d-5p, while examples of miRNA for which expression was particularly decreased included hsa-miR-145-5p, hsa-miR-181a-5p, hsa-miR-29b-3p, hsa-miR-34a-5p, hsa-miR-199b-5p and hsa-miR-503-5p.

(Test 5) Secretion of Cytokines into Culture Supernatant

After conditioning umbilical cord-derived mesenchymal stem cells (UC-MSC: Umbilical Cord-derived Mesenchymal Stem Cells Wharton's Jelly (HMSC-WJ), FC-0020, Lifeline Corp.) with the recommended medium of Lifeline Corp. under conditions of 37° C. and 5% $CO_2$, the medium was replaced with the recommended medium of Lifeline Corp. or the formulated medium ($1\times10^5$ cells/well, 6-well plate). The cells were re-seeded after culturing for 8 days after changing each medium followed by replacing with 0.2% FBS-containing DMEM/F12 on the following day and recovering the culture supernatant two days layer (after 48 hours). The levels of decorin, osteoprotegerin and MMP1 in the recovered supernatant were measured by ELISA. The results are shown in FIG. 15.

Figure 15:
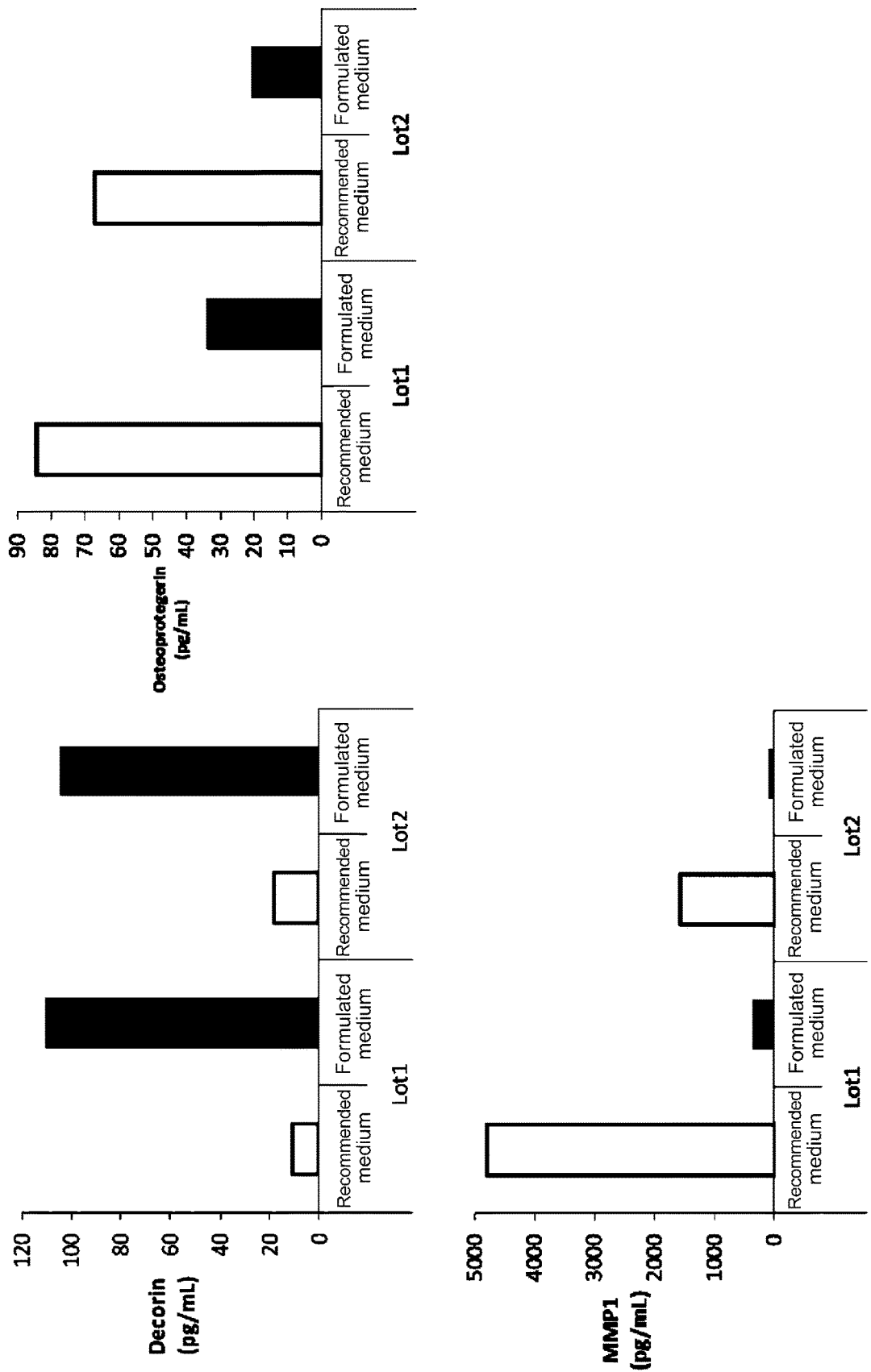
FIG. 15 depicts bar graphs indicating concentrations of decorin, osteoprotegerin and MMP1 in the culture supernatant of umbilical cord-derived mesenchymal stem cells obtained by culturing in formulated medium or recommended medium.

As shown in FIG. 15, decorin, osteoprotegerin and MMP1 were contained in the culture supernatant of UC-MSC cultured in the formulated medium, the content of decorin was higher in comparison with the culture supernatant of UC-MSC cultured in the recommended medium, while conversely the contents of osteoprotegerin and MMP1 were lower.

(Test 6) Induction of Oxidative Stress Resistance

Umbilical cord-derived mesenchymal stem cells (UC-MSC: Umbilical Cord-derived Mesenchymal Stem Cells Wharton's Jelly (HMSC-WJ), FC-0020, Lifeline Corp.;

UC-MSC: Umbilical Cord-Derived Mesenchymal Stem Cells, Sciencell Research Laboratories, Inc.; and Umbilical Cord-Derived Mesenchymal Stem Cells, ATCC) were conditioned with the recommended medium of each manufacturer under conditions of 37° C. and 5% $CO_2$ followed by replacing the medium with the recommended medium of each manufacturer or the formulated medium ($0.3 \times 10^5$ cells/well to $1 \times 10^5$ cells/well, 6-well plates). After subculturing every 2 to 3 days, the cultured cells were treated with various concentrations of rotenone (0 nM, 100 nM, 200 nM, 500 nM and 1 µM). The cells were stained with Hoechst 33342 48 hours later followed by counting the number of nuclei with ImageXpress. The results are shown in FIG. 16.

Figure 16:
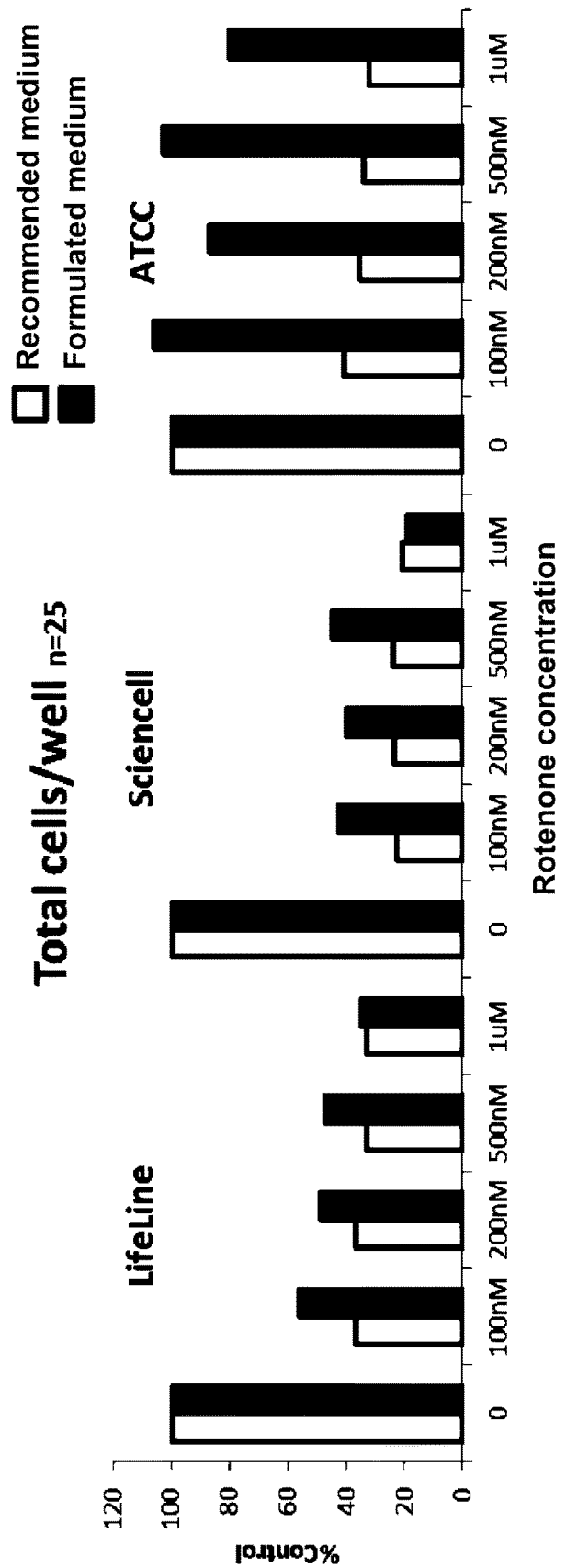
FIG. 16 depicts bar graphs indicating a comparison of oxidative stress resistance among umbilical cord-derived mesenchymal stem cells obtained by culturing in formulated medium or recommended medium.

As shown in FIG. 16, although UC-MSC demonstrated a decrease in the number of cells as a result of concentration-dependent impairment by rotenone, as a result of culturing the cells in the formulated medium, the cells acquired resistance to damage by rotenone treatment and became less susceptible to oxidative stress, which suggested the potential to inhibit decreases in the number of cells.

(Test 7) Effects of Culture Supernatant on Enhancing Barrier Function

Umbilical cord-derived mesenchymal stem cells (UC-MSC: Umbilical Cord-derived Mesenchymal Stem Cells Wharton's Jelly (HMSC-WJ), FC-0020, Lifeline Corp.) were conditioned with the recommended medium of Lifeline Corp. under conditions of 37° C. and 5% $CO_2$ followed by replacing the medium with the recommended medium of Lifeline Corp. or the formulated medium ($1 \times 10^5$ cells/well, 6-well plates). After replacing the medium with each medium and culturing for 8 days, the medium was replaced with 10% FCS-containing DMEM/F-12 medium at 2 ml/well. The culture supernatant (Sup-1) was recovered one day later, 2 ml aliquots of fresh medium were dispensed into each well and culturing was continued. The supernatant (Sup-2) was again recovered 24 hours later.

Human colon cancer-derived cell line Caco-2 was subcultured in 10% FCS-containing DMEM medium and cells from the third passage were used in the present test. Caco-2 cells were seeded into a Transwell plate (Corning Costar Corp.) at $5 \times 10^4$ cells/well, and the media was removed on the following day after confirming that the cells had adhered to the Transwell. The aforementioned culture supernatant (Sup-1) of the umbilical cord-derived mesenchymal stem cells was diluted 10-fold with 10% FCS-containing DMEM medium and added to the Transwell plate. After removing the medium on the following day, the aforementioned culture supernatant (Sup-2) of the umbilical cord-derived mesenchymal stem cells was diluted 4-fold with 10% FCS-containing DMEM medium and added to the Transwell plate. Moreover, IL-1β was added at 1.5 ng/ml, and after additionally culturing for 20 hours, transepithelial electric resistance (TER) was measured. The number (absorbance) of Caco-2 cells cultured under the same conditions was measured with a cell growth assay kit (WST-8, Dojindo Laboratories, #343-07623), and the values obtained by dividing the resulting TER value by the number of cells (TER value) are shown in FIG. 17.

Figure 17:
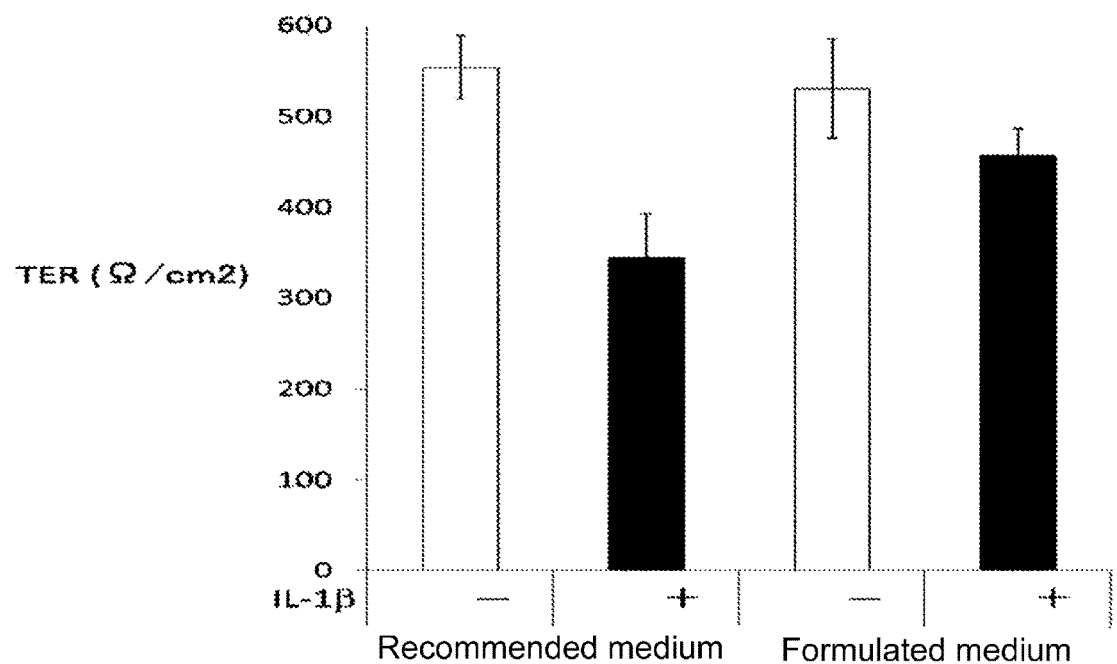
FIG. 17 is a bar graph indicating the barrier function enhancing activity of culture supernatants of umbilical cord-derived mesenchymal stem cells obtained by culturing in formulated medium or recommended medium.

As shown in FIG. 17, cell-to-cell barrier strength of the Caco-2 cells underwent a decrease as a result of IL-1β treatment. In contrast, the addition of the culture supernatant of UC-MSC cultured in the formulated medium demonstrated a recovery of TER values in comparison with the case of adding the culture supernatant of UC-MSC cultured in recommended medium. On the basis of this result, a culture supernatant of ROR1-positive UC-MSC cultured in the formulated medium was determined to demonstrate superior barrier function enhancing effects.

(Test 8) Anti-Inflammatory Effect

Umbilical cord-derived mesenchymal stem cells (UC-MSC: Umbilical Cord-derived Mesenchymal Stem Cells Wharton's Jelly (HMSC-WJ), FC-0020, Lifeline Corp.) were conditioned with the recommended medium of Lifeline Corp. under conditions of 37° C. and 5% $CO_2$ followed by replacing the medium with the recommended medium of Lifeline Corp. or the formulated medium ($1 \times 10^5$ cells/well, 6-well plates). Cells obtained after replacing the medium with each medium and culturing for 8 days were used in the testing indicated below.

A medium was prepared by diluting a 0.5 mM DMSO solution of Calcein-AM staining reagent 1,000-fold with 10% FCS DMEM. The Calcein-AM-containing medium was added to mouse macrophage cell line Raw264.7, and after pre-culturing for 3 hours at 37° C. in 5% $CO_2$, the cells were seeded in a 48-well plate at $5 \times 10^5$ cells/well.

On the following day, UC-MSC cultured in the aforementioned recommended medium or formulated medium were added at $5 \times 10^3$ cells/well followed by initiation of co-culturing of the UC-MSC and Raw264.7 cells. LPS was added at 100 ng/mL 4 hours after the start of co-culturing. The culture supernatant was collected 17 to 18 hours later. The amount of IL-6 present in the culture supernatant was measured by ELISA (mIL-6 ELISA, R&D Duoset ELISA Kit, R&D Systems Inc., DY406-05). Furthermore, after recovering the culture supernatant, the number of cells corresponding to the amount of IL-6 was corrected by measuring the fluorescence value of Calcein-AM preliminarily taken up by the Raw264.7 cells and subtracting that value. The results are shown in FIG. 18.

Figure 18:
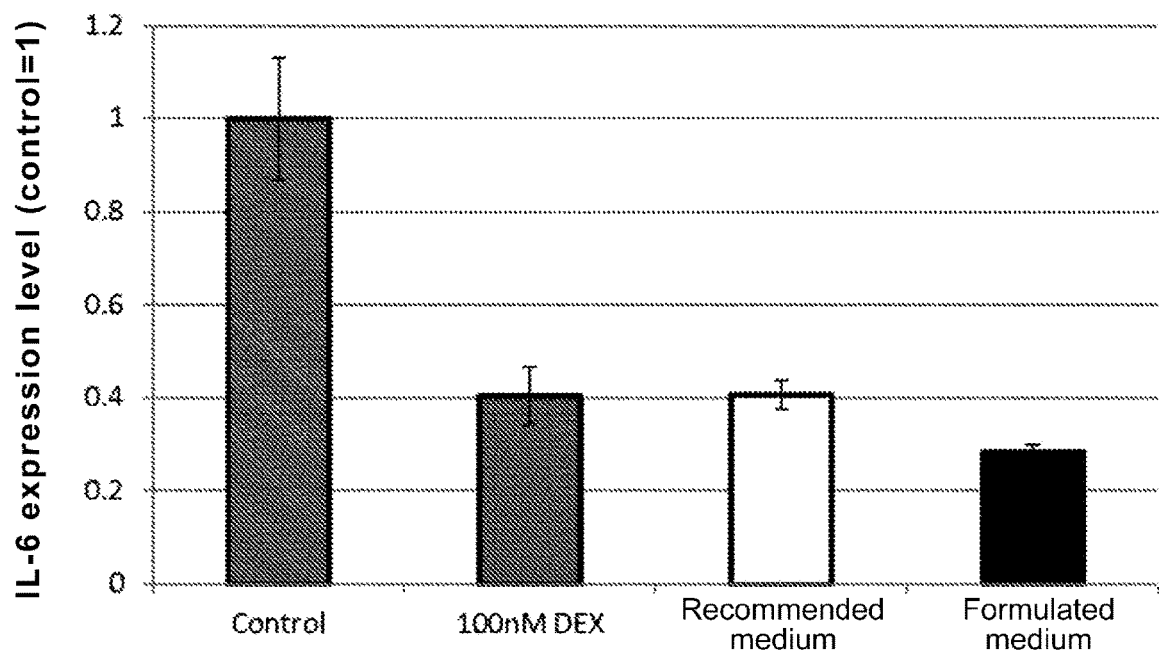
FIG. 18 is a bar graph indicating the inflammatory cytokine production inhibitory effect of umbilical cord-derived mesenchymal stem cells obtained by culturing in formulated medium or recommended medium.

As shown in FIG. 18, as a result of co-culturing with the UC-MSC, production of inflammatory cytokine produced by mouse macrophage cell line Raw264.7 in the form of IL-6 was inhibited. In addition, that inhibitory effect was significantly higher for ROR1-positive UC-MSC cultured in the formulated medium in comparison with UC-MSC cultured in the recommended medium.

(Test 9) Bone Differentiation Capacity

Umbilical cord-derived mesenchymal stem cells (UC-MSC: Umbilical Cord-derived Mesenchymal Stem Cells Wharton's Jelly (HMSC-WJ), FC-0020, Lifeline Corp.) and adipose-derived mesenchymal stem cells (AD-MSC: Adipose-Derived Mesenchymal Stem Cells, FC-0034, Lifeline Corp.) were conditioned with the recommended medium of Lifeline Corp. under conditions of 37° C. and 5% $CO_2$ followed by replacing the medium with the Lifeline recommended medium or formulated medium ($1 \times 10^5$ cells/well, 6-well plates). The cells were subcultured every 2 to 3 days to prepare cells of 8 passages. After having been subcultured for 8 passages, both types of MSC were seeded in two Cell BIND T-75 flasks each at 7000 cells/$cm^2$ followed by replacing the medium in one of the MSC flasks with the formulated medium while continuing culturing to 90% to 100% confluency in the recommended medium in the other flask. After re-subculturing for a ninth passage, the cells were re-seeded in four T-75 flasks each, and the cells were used in the differentiation test described below 8 days after grouping (10 passages).

The cells of each group were recovered on day 8 after grouping and seeded in a 24-well plate (Cell Bind 3337, Corning Inc.) using osteocyte differentiation medium for human mesenchymal stem cells (Complete Osteogenesis Medium, Lifeline Corp., LM-0023) at the cell density recommended in the Kurabo differentiation protocol. Culturing for inducing bone differentiation consisted of replacing the medium 48 hours after seeding in the differentiation medium followed by replacing the medium every 3 to 4 days thereafter for 28 days. The staining method consisted of washing the wells used for staining once with PBS starting on day 21 after seeding, followed by adding anhydrous ethanol and allowing to stand at room temperature for 30 minutes to fix the cells. The anhydrous ethanol was aspirated from the wells followed by allowing the wells to dry by allowing to stand undisturbed for about 30 minutes in a laminar flow cabinet. After adding 2% Alizarin red solution and allowing to stand undisturbed for 15 minutes at room temperature, the wells were washed twice with distilled water (DW) and allowed to dry. Photographs of the stained cells were captured using a microscope (Olympus IX70). The results of Alizarin red staining are shown in FIG. 19.

Figure 19:
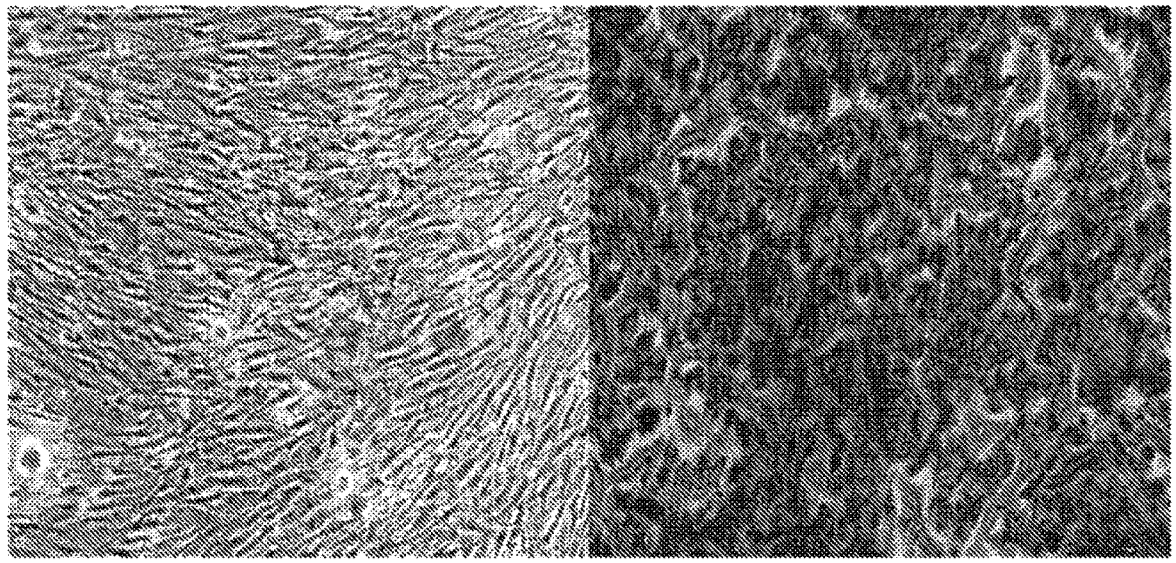
FIG. 19 depicts photomicrographs indicating the differentiation of mesenchymal stem cells (adipose-derived and umbilical cord-derived) cultured in formulated medium, and mesenchymal stem cells (both adipose-derived and umbilical cord-derived) cultured in recommended medium, into osteocytes.
Figure 19:
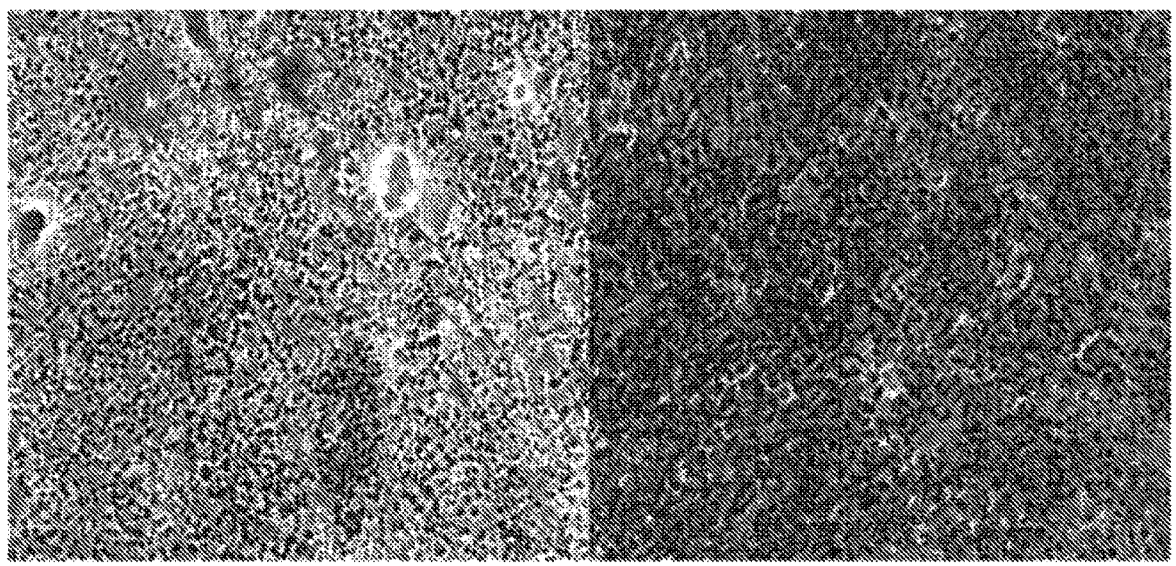

As shown in FIG. 19, UC-MSC and AD-MSC cultured in the formulated medium were determined to have a greater capacity for differentiation into bone in comparison with the case of culturing in the recommended medium.

(Test 10) Adipose Differentiation Capacity

Preparation of the mesenchymal stem cells used in the differentiation experiment was carried out using the same method as Test 9.

The cells of each group were recovered on day 8 after grouping and seeded in a 24-well plate (Cell Bind 3337, Corning Inc.) using differentiation medium (adipocyte differentiation medium for human mesenchymal stem cells: AdipoLife DfKt-1 (Lifeline Corp., LL-0050) or AdipoLife DfKt-2 (Lifeline Corp., LL-0059)) at the cell density recommended in the Kurabo differentiation protocol. Culturing for inducing adipose differentiation consisted of replacing the medium 48 hours after seeding for differentiation culturing followed by replacing the medium every 3 to 4 days thereafter for 28 days. The staining method consisted of washing the wells used for staining once with PBS starting on day 21 after seeding, followed by washing twice with 4% (v/v) paraformaldehyde-phosphate buffer solution so as to leave behind a small amount of the medium. The 4% (v/v) paraformaldehyde-phosphate buffer solution was added again followed by allowing to stand undisturbed for 20 minutes at room temperature. Subsequently, the wells were washed twice with distilled water (DW) so as to leave behind a small amount of the medium followed by washing once with 100% isopropanol. A stock solution of Oil Red O stain diluted to 60% with distilled water (DW) was then added followed by allowing to stand undisturbed for 30 minutes at 37° C. and then completely aspirating off the solution. 60% isopropanol was then added followed by the addition of distilled water after waiting for about 10 seconds. After washing twice with distilled water (DW), the cells were photographed with a microscope (Olympus IX70). Furthermore, the AdipoLife BM (100 ml) of the AdipoLife DfKt-1 medium was divided into 15 ml and 85 ml aliquots, DifFactor 1 (1 ml) was added to the 15 ml aliquot to obtain a differentiation initiation medium for AD-MSC, while DifFactor 2 (5 ml) was added to the 85 ml aliquot to obtain a differentiation maintenance medium for AD-MSC. In addition, DifFactor 3 (10 ml) was added to AdipoLife BM (100 ml) of the AdipoLife DfKt-2 medium to obtain a differentiation medium for UC-MSC. The results of Oil Red O staining are shown in FIG. 20.

Figure 20:
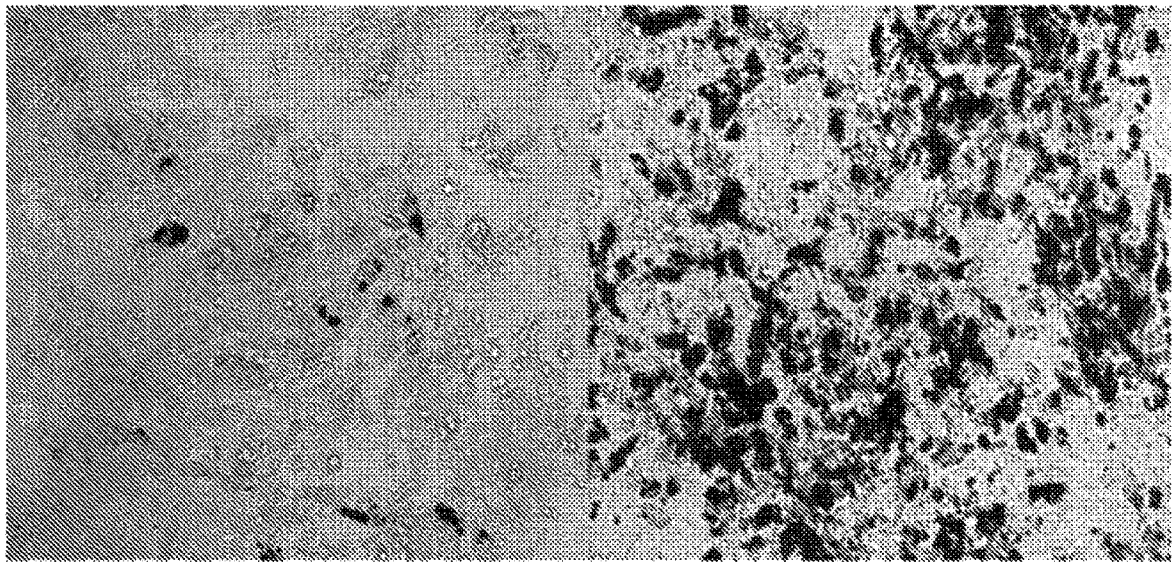
FIG. 20 depicts photomicrographs indicating the differentiation of mesenchymal stem cells (adipose-derived and umbilical cord-derived) cultured in formulated medium, and mesenchymal stem cells (both adipose-derived and umbilical cord-derived) cultured in recommended medium, into adipocytes.
Figure 20:
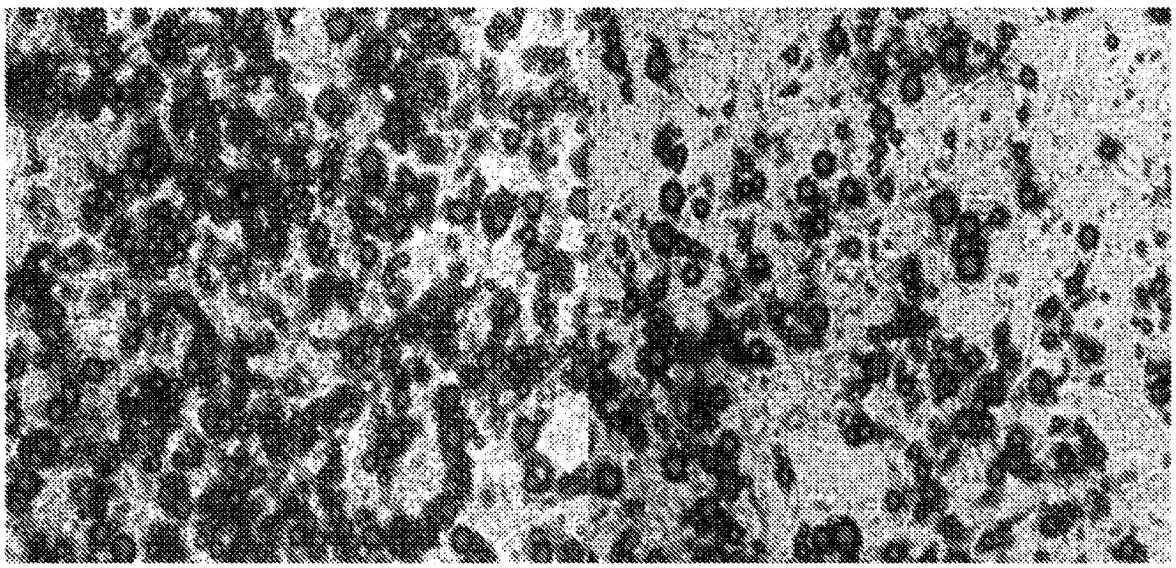

As shown in FIG. 20, UC-MSC cultured in the formulated medium were determined to have a greater capacity for differentiation into adipocytes in comparison with UC-MSC cultured in the recommended medium. On the other hand, AD-MSC cultured in the recommended medium were determined to have a somewhat high capacity for differentiation into adipocytes.

(Test 11) Differentiation into Chondrocytes

Preparation of the mesenchymal stem cells used in the differentiation experiment was carried out using the same method as Test 9.

The cells of each group were recovered on day 8 after grouping and seeded in a 24-well plate (3527, Corning Inc.) using differentiation medium (chondrocyte differentiation medium for human mesenchymal stem cells: ChondroLife Complete Chondrogenesis Medium (Lifeline Corp., LM-0023)) at the cell density recommended in the Kurabo differentiation protocol. Culturing for inducing cartilage differentiation consisted of seeding the cells according to the micromass method. More specifically, the recovered cells were concentrated in each maintenance medium to $1.6 \times 10^7$ cells/ml and dropped into a 24-well plate (3526, Corning Inc.) at 4 drops of 5 μl aliquots/well, and after allowing to stand undisturbed for 2 hours at 37° C. and 5% $CO_2$, chondrocyte differentiation medium was added at 500 μl/well. Subsequently, the medium was replaced every 3 days for 21 days. The staining method consisted of washing the wells used for staining once with PBS starting on day 21 after seeding, followed by adding 10% neutral-buffered formalin and allowing to stand for 30 minutes at room temperature to fix the cells. Subsequently, the wells were washed once with distilled water (DW) followed by the addition of 3% acetic acid and allowing to stand undisturbed for 1 minute. After adding Alcian Blue staining solution and allowing to stand undisturbed for 20 minutes at room temperature, the staining solution was aspirated and followed by the addition of 3% acetic acid and waiting for 3 minutes. Finally, the wells were washed twice with distilled water (DW) and photographed with a digital camera.

As a result of the above testing, although there were no well-defined differences in the capacity to differentiate into chondrocytes between cells cultured in the formulated medium and cells cultured in the recommended medium, the cells formed small aggregates in the case cultured in the formulated medium, whereas many of the cells stayed flat on the plate in the case cultured in the recommended medium.

<Examination of Function of ROR1-Positive MSC>

ROR1-positive MSC (F posi) and ROR1-negative MSC (F nega) were isolated by sorting from a cell population obtained by culturing in the aforementioned formulated medium, and their respective functions were examined using ROR1-positive MSC and ROR1-negative MSC mixed at a ratio of 1:1 (F mix) and MSC on which sorting was not carried out (F unsorted) as necessary. The following provides a detailed explanation thereof.

Umbilical cord-derived mesenchymal stem cells (UC-MSC: Umbilical Cord-derived Mesenchymal Stem Cells Wharton's Jelly (HMSC-WJ), FC-0020, Lifeline Corp.) were cultured in the aforementioned formulated medium to obtain a cell population containing numerous ROR1-positive MSC. ROR1-positive MSC and ROR1-negative MSC were obtained from the resulting cell population by cell sorting. More specifically, PE anti-human ROR1 (BD Biosciences Inc., #564474) or mouse IgG2b PE, κ isotype control (Biolegend Inc., #401208) was respectively added at a concentration of 5 μl/100 μl to the resulting MSC cultured in the formulated medium and allowed to react for 1 hour. The cells were washed 3 times with 1% BSA/D-PBS solution, re-suspended in 1% BSA/D-PBS and then subjected to cell sorting with the Sony SH800Z. Each cell group, and as necessary, ROR1-positive MSC and ROR1-negative MSC mixed at a ratio of 1:1 (F mix) and MSC on which sorting was not carried out (F unsorted), were seeded in a 6-well plate or 96-well plate at $1\times10^4$ cells/cm$^2$ to $3\times10^4$ cells/cm$^2$ using the aforementioned formulated medium for use in the testing indicated below.

(Cell Migration Test)

The ROR1-positive MSC (F posi) and ROR1-negative MSC (F nega) obtained in the manner described above were each cultured for 48 hours in 0.2% FBS-DMEM/F12 medium followed by recovery of the culture supernatants and comparing the cancer cell migration inhibitory capacity of each culture supernatant. B16 mouse melanoma cells were used for the cancer cells. More specifically, B16 mouse melanoma cells cultured to sub-confluency were recovered using 0.25% trypsin/EDTA solution (Gibco Corp.). The recovered cells were suspended in DMEM/F12 medium (containing 0.2% FBS and 1% antibiotic/antimycotic) and seeded in 200 µL of medium in the upper compartment wells of a 24-well Boyden chamber (Corning Inc., 3422) in aliquots of about $4.0\times10^4$ cells each. 550 µL of each MSC culture supernatant prepared in the above manner were added to the lower compartment wells followed by culturing for 6 hours at 37° C. in an environment containing 5% carbon dioxide gas and 95% air. Subsequent treatment was carried out in the same manner as the experiment of FIG. 1. The results are shown in FIG. 21.

Figure 21:
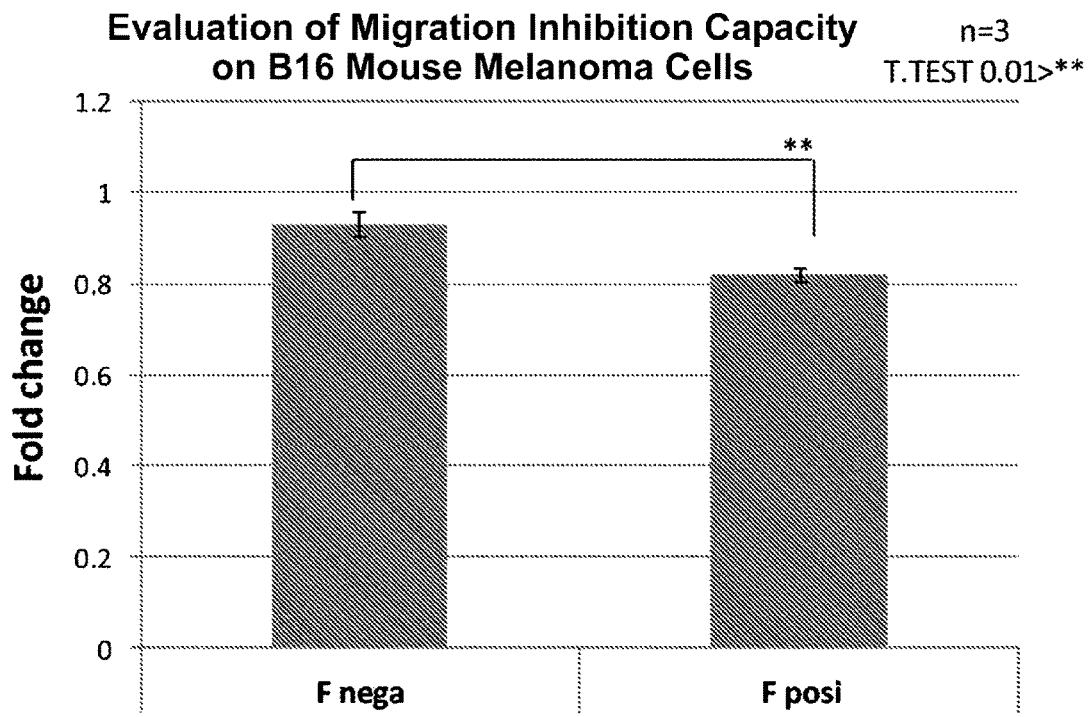
FIG. 21 is a bar graph indicating the demonstration of cancer cell migration inhibitory effects by a culture supernatant of ROR1-positive mesenchymal stem cells.

As shown in FIG. 21, the culture supernatant of ROR1-positive MSC was determined to demonstrate an extremely high capacity to inhibit the migration of the cancer cells (B16 mouse melanoma cells) in comparison with the culture supernatant of ROR1-negative MSC. Thus, ROR1-positive MSC and/or a culture supernatant thereof were thought to demonstrate a superior effect in inhibiting the infiltration and metastasis of cancer cells, and a pharmaceutical composition containing the same was suggested to be effective in the treatment and prevention of cancer.

(Oxidative Stress Resistance Test)

Each of the ROR1-positive MSC (F posi), ROR1-negative MSC (F nega), ROR1-positive MSC and ROR1-negative MSC mixed at a ratio of 1:1 (F mix) and MSC not subjected to sorting (F unsorted) obtained according to the aforementioned method were re-seeded after aligning cell density followed by treating for 1 hour with various concentrations of $H_2O_2$/HBSS solution (0 µM, 100 µM, 200 µM and 400 µM) two days later, washing twice with HBSS(+), and comparing the numbers of cells 24 hours after returning to the original medium by nuclear staining with Hoechst 33342 (Dojindo #H342; 1 µg/ml, 5 to 10 minutes) followed by analysis of fluorescence images thereof.

Figure 22:
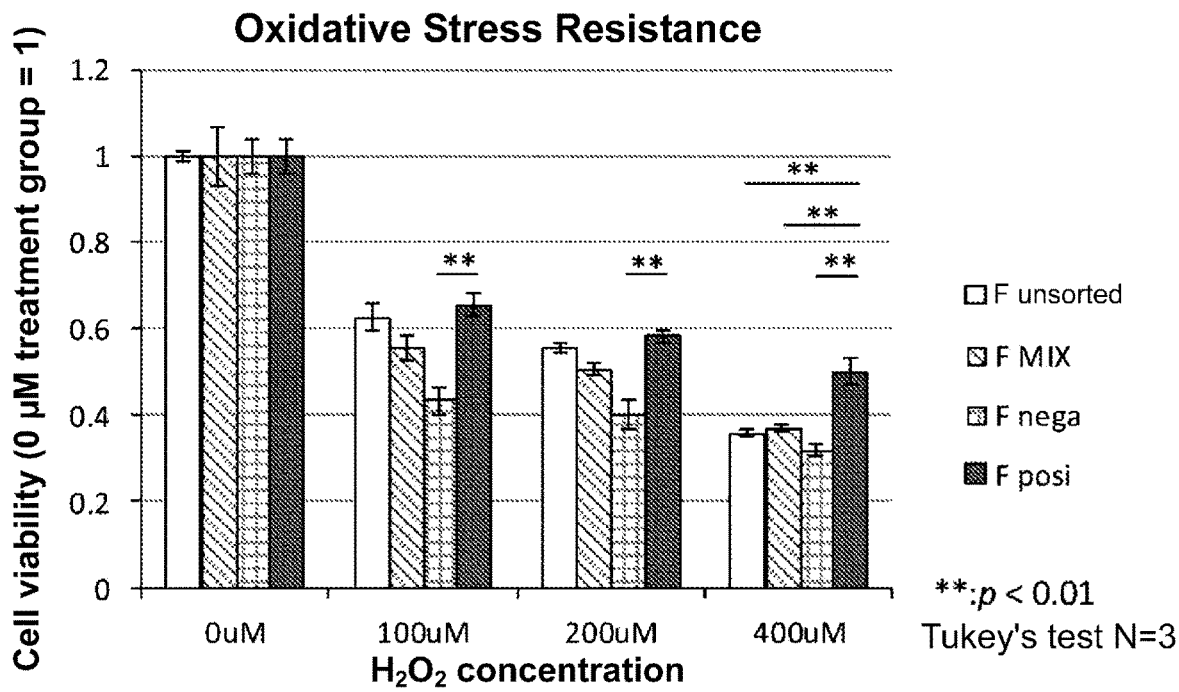
FIG. 22 is a bar graph indicating the demonstration of oxidative stress resistance by a culture supernatant of ROR1-positive mesenchymal stem cells.

As shown in FIG. 22, although the UC-MSC demonstrated a reduction in the number of cells as a result of being impaired by the $H_2O_2$/HBSS treatment solution, resistance to impairment by treatment with $H_2O_2$/HBSS solution of the ROR1-positive MSC (F posi) was significantly higher in comparison with the ROR1-negative MSC (F nega) and tended to also be sufficiently high in comparison with the ROR1-positive MSC and ROR1-negative MSC mixed at a ratio of 1:1 (F mix) and MSC not subjected to sorting (F unsorted), thereby suggesting inhibition of reductions in the number of cells.

(Mitochondrial Transfer Test)

Each of the ROR1-positive MSC (F posi), ROR1-negative MSC (F nega), ROR1-positive MSC and ROR1-negative MSC mixed at a ratio of 1:1 (F mix) and MSC not subjected to sorting (F unsorted) obtained according to the aforementioned method were seeded in a 6-well plate followed by a comparison of the mitochondrial transfer capacity of each of the cells using the same method as that of the previously described mitochondrial transfer test. The following cells were used as recipient cells.

NHDF cells (human dermal fibroblasts): Human Dermal Fibroblast (Kurabo, KF-4009); furthermore, a combination of DMEM medium (Gibco Corp., 11995-065), 10% FCS and 1% AB* was used to culture the NHDF cells.

BSMC-COPD cells (human bronchial smooth muscle cells of chronic obstructive pulmonary disease: Bronchial Smooth Muscle Cell Chronic Obstructive Pulmonary Disease (Lonza Group Ltd., 00195274); furthermore, a combination of SmGMTM-2 medium, Bullet Kit (Lonza Group Ltd., CC-3182) and 1% antibiotic-antimycotic (Gibco Corp.) was used to culture the BSMC-COPD cells.

HCM (human cardiac myocytes): Human Cardiac Myocytes (HCM, PromoCell GmbH)); furthermore, Myocyte Basal Medium (PromoCell GmbH, C-22170) and Myocyte Growth Medium Supplement Pack (PromoCell GmbH, C-39270) were used to culture the HCM.

Figure 23:
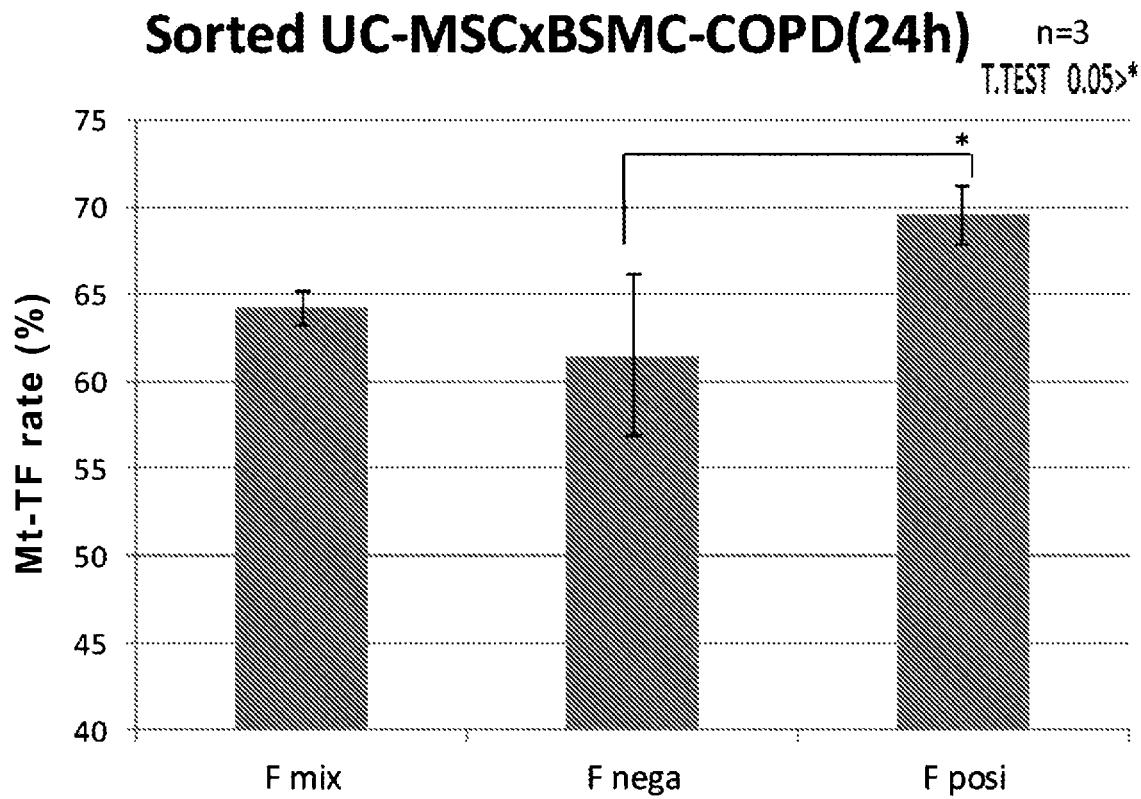
FIG. 23 is a bar graph indicating the mitochondrial transfer capacity of ROR1-positive mesenchymal stem cells in human bronchial smooth muscle cells of chronic obstructive pulmonary disease.
Figure 24:
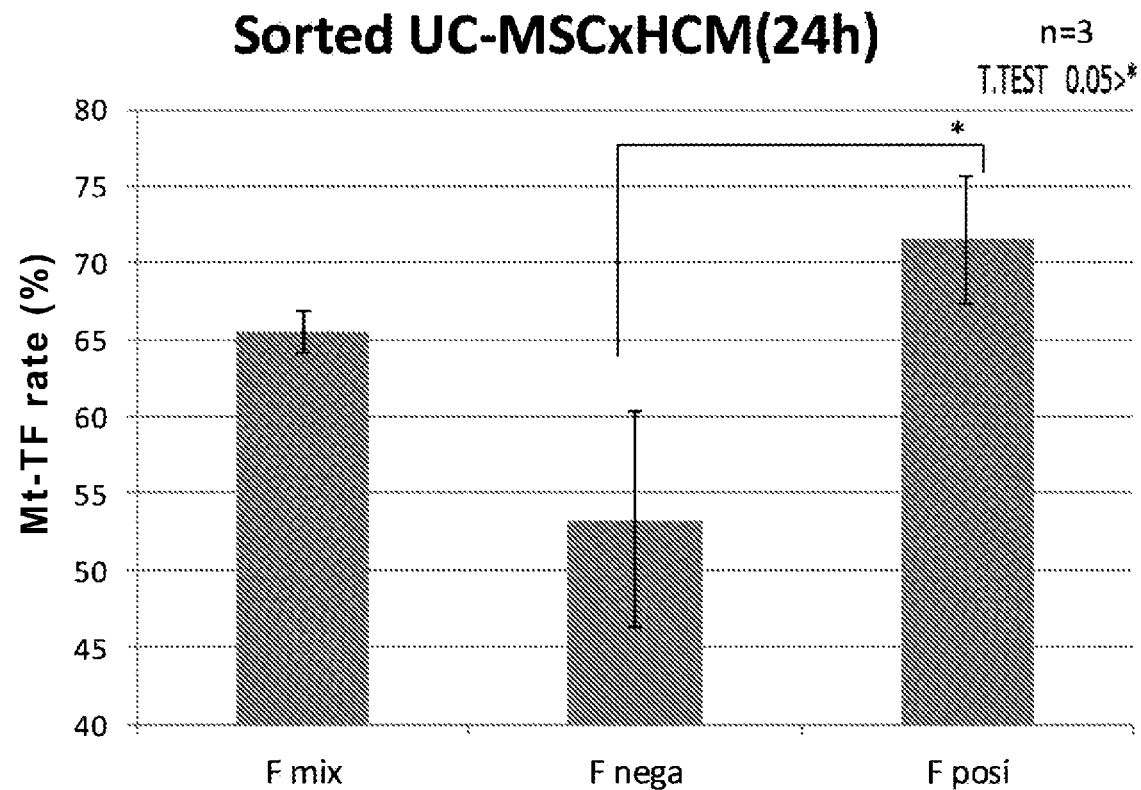
FIG. 24 is a bar graph indicating the mitochondrial transfer capacity of ROR1-positive mesenchymal stem cells in human cardiac myocytes.

As shown in FIGS. 23 and 24, mitochondrial transfer rates to BSMC-COPD cells (human bronchial smooth muscle cells of chronic obstructive pulmonary disease) and HCM cells (human cardiac myocytes) were determined to be considerably higher for ROR1-positive MSC (F posi) in comparison with ROR1-negative MSC (F nega) and ROR1-positive MSC and ROR1-negative MSC mixed at a ratio of 1:1 (F mix). In addition, although the data is not shown, the mitochondrial transfer rate to NHDF cells (human dermal fibroblasts) tended to be sufficiently high for ROR1-positive MSC (F posi) in comparison with ROR1-negative MSC (F nega) and ROR1-positive MSC and ROR1-negative MSC mixed at a ratio of 1:1 (F mix).

On the basis of the above results, ROR1-positive MSC were determined to demonstrate superior migration capacity as well as potent resistance to oxidative stress. In addition, since ROR1-positive MSC demonstrate considerably high rates of transferring their own mitochondria to human dermal fibroblasts in the form of NHDF cells, human bronchial smooth muscle cells of chronic obstructive pulmonary disease in the form of BSMC-COPD cells and human cardiac myocytes in the form of HCM cells, ROR1-positive MSC are thought to be effective for treating or preventing fibrosis, chronic obstructive pulmonary disease and heart disease. In addition, ROR1-positive MSC are considered to also be able to be widely used against symptoms accompanying diseases and aging associated with impaired mitochondrial function or decreased mitochondrial activity in addition to the aforementioned diseases.

The invention claimed is:

1. A method for treating fibrosis, comprising administering ROR1-positive mesenchymal stem cells derived from umbilical cord tissue and/or a supernatant thereof proliferated in formulated medium,
   wherein the RORI-positive mesenchymal stem cells are positive for CD29, CD73, CD90, CD I 05 and CD 166, and
   wherein the formulated medium comprises at least two types of components selected from the group consisting of PTEN inhibitors, p53 inhibitors, p38 inhibitors, Wnt signaling activators and ROCK inhibitors.

2. The method for treating fibrosis of claim 1, wherein the formulated medium comprises a PTEN inhibitor in a concentration ranging from 10 nM to 10 µM, a p53 inhibitor in a concentration ranging from 100 nM to 1 mM, a p38 inhibitor in a concentration ranging from 1 nM to 1 µM, a Wnt signaling activator in a concentration ranging from 1 µM to 10 mM and a ROCK inhibitor in a concentration ranging from 1 nM to 10 µM.

* * * * *

UNITED STATES PATENT AND TRADEMARK OFFICE
CERTIFICATE OF CORRECTION

PATENT NO. : 11,707,488 B2
APPLICATION NO. : 15/755859
DATED : July 25, 2023
INVENTOR(S) : Ikeyama et al.

Page 1 of 1

It is certified that error appears in the above-identified patent and that said Letters Patent is hereby corrected as shown below:

In the Claims

At Column 38, Claim number 1, Line number 50, "CD I 05" should read -- CD105 --.

Signed and Sealed this
Thirteenth Day of February, 2024

Katherine Kelly Vidal
*Director of the United States Patent and Trademark Office*